US009561065B2

(12) United States Patent
Privitera et al.

(10) Patent No.: US 9,561,065 B2
(45) Date of Patent: Feb. 7, 2017

(54) ROBOTIC TOOLKIT

(71) Applicant: AtriCure, Inc., Mason, OH (US)

(72) Inventors: Salvatore Privitera, Mason, OH (US); Matthew Monti, Cincinnati, OH (US); William J. Abner, Marlborough, MA (US); Adam Harp, Cincinnati, OH (US); Jeffrey W. Stone, Lebanon, OH (US)

(73) Assignee: AtriCure, Inc., Mason, OH (US)

( * ) Notice: Subject to any disclaimer, the term of this patent is extended or adjusted under 35 U.S.C. 154(b) by 0 days.

(21) Appl. No.: 14/748,755

(22) Filed: Jun. 24, 2015

(65) Prior Publication Data

US 2015/0289919 A1    Oct. 15, 2015

Related U.S. Application Data

(63) Continuation of application No. 13/477,761, filed on May 22, 2012, now Pat. No. 9,066,741, which is a
(Continued)

(51) Int. Cl.
*A61B 18/18* (2006.01)
*A61B 18/02* (2006.01)
(Continued)

(52) U.S. Cl.
CPC ........... *A61B 18/02* (2013.01); *A61B 18/1445* (2013.01); *A61B 34/30* (2016.02); *A61B 18/1402* (2013.01);
(Continued)

(58) Field of Classification Search
CPC . A61B 18/02; A61B 18/1402; A61B 18/1445; A61B 19/2203; A61B 2017/00477; A61B 2017/2945; A61B 34/30
See application file for complete search history.

(56) References Cited

U.S. PATENT DOCUMENTS

| 5,334,181 A * | 8/1994 | Rubinsky et al. ............... 606/22 |
| 5,452,582 A * | 9/1995 | Longsworth .................. 62/51.2 |
| 2011/0230894 A1* | 9/2011 | Simaan et al. ................ 606/130 |

* cited by examiner

*Primary Examiner* — George Manuel
(74) *Attorney, Agent, or Firm* — Porter Wright Morris & Arthur LLP; Ryan Willis

(57) ABSTRACT

A surgical instrument kit comprising: (a) a robotic arm comprising a first jaw including a first bipolar electrode and a second jaw including a second bipolar electrode, wherein at least one of first jaw and second jaw is repositionable with respect to the other jaw; (b) a first surgical tool head including a first electrical load in electrical communication with a first pair of electrical terminals, the first surgical tool head adapted to be removably coupled to the robotic arm; and, (c) a second surgical tool head including a second electrical load in electrical communication with a second pair of electrical terminals, the second surgical tool head adapted to be removably coupled to the robotic arm, where the first pair of electrical terminals of the first surgical tool head are adapted to engage the first bipolar electrode and the second bipolar electrode to establish electrical communication between the first bipolar electrode and a first of the first pair of electrical terminals and between the second bipolar electrode and a second of the first pair of electrical terminals, and where the second pair of electrical terminals of the second surgical tool head are adapted to engage the first bipolar electrode and the second bipolar electrode to establish electrical communication between the first bipolar elec- trode and a first of the second pair of electrical terminals and between the second bipolar electrode and a second of the second pair of electrical terminals.

16 Claims, 28 Drawing Sheets

Related U.S. Application Data continuation of application No. 13/286,554, filed on Nov. 1, 2011, now abandoned.

(60) Provisional application No. 61/408,993, filed on Nov. 1, 2010.

(51) Int. Cl.
  *A61B 18/14*    (2006.01)
  *A61B 17/00*    (2006.01)
  *A61B 17/29*    (2006.01)

(52) U.S. Cl.
  CPC ............... *A61B 2017/00477* (2013.01); *A61B 2017/2945* (2013.01)

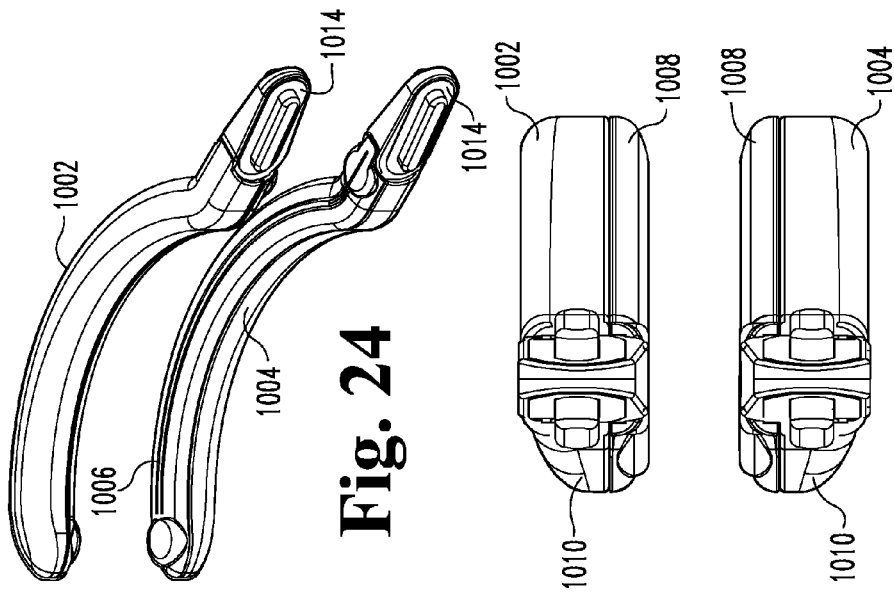
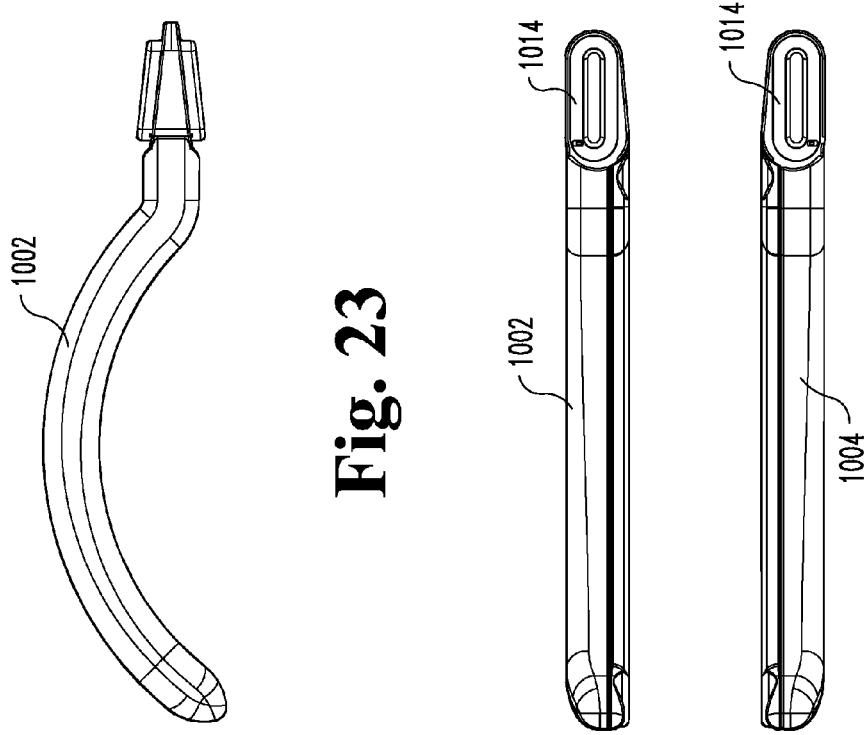

ROBOTIC TOOLKIT

CROSS REFERENCE TO RELATED APPLICATIONS

This application is a continuation of, and claims priority under 35 U.S.C. §120 to, U.S. patent application Ser. No. 13/477,761, filed May 22, 2012, now U.S. Pat. No. 9,066,741, which was a continuation of U.S. patent application Ser. No. 13/286,554, filed Nov. 1, 2011, now abandoned, which claimed priority to U.S. patent application Ser. No. 61/408,993, filed Nov. 1, 2010, now expired, the disclosures of which are incorporated herein by reference.

RELATED ART

Field of the Invention

The present invention is directed to surgical instruments and, more specifically but not exclusively, to robotic surgical instruments and methods for their use that may comprise part of a toolkit.

INTRODUCTION TO THE INVENTION

Some tool heads disclosed and described herein are particularly, but not exclusively, suited for use in cardiac ablation procedures for the treatment of atrial fibrillation using electro-surgical RF energy, cryothermia, or some other energy, as shown and described for example in U.S. Pat. No. 6,546,935, which is incorporated herein by reference, as well as the related exclusion or occlusion of the left atrial appendage by stapler or clip.

During the performance of cardiac ablation procedures, various instruments may be used to create transmural lines of ablation in tissue, such as an ablation clamp having opposed jaw members having opposed electrodes thereon, an ablation "pen", a linear pen, a surgical dissector, a surgical clip, and a cryoablation probe. Such instruments are shown generally in U.S. Pat. No. 7,113,831 and U.S. Published Patent Application No. 2006/0084974 (showing an ablation clamp with opposed jaw members), U.S. Published Patent Application Nos. 2006/0161147 and 2006/0161149 (showing an ablation pen), U.S. Published Patent Application No. 2006/0161151 (showing a linear pen), U.S. Published Patent Application No. 2005/0203561 (showing a lighted dissector), U.S. Pat. No. 7,645,285 (showing a surgical clip), and U.S. Published Patent Application No. 20100241114 (a cryogenic probe), all of which are incorporated herein by reference. In another procedure, a clip may be applied externally to the left atrial appendage (LAA) to reduce the risks of clot generation associated with the LAA or the appendage may be surgically stapled using an automatic linear stapler (See U.S. Pat. No. 6,302,311—Boston Scientific). Such a clip and clip applicator are shown in U.S. application Ser. No. 12/033,935, filed Feb. 20, 2008, which is also incorporated herein by reference. Each of the aforementioned devices or tools is typically carried on its own dedicated hand piece and a shaft, with the operating head at the distal end thereof.

It is a first aspect of the present invention to provide a surgical instrument kit comprising: (a) a robotic arm comprising a first jaw including a first bipolar electrode and a second jaw including a second bipolar electrode, wherein at least one of first jaw and second jaw is repositionable with respect to the other jaw; (b) a first surgical tool head including a first electrical load in electrical communication with a first pair of electrical terminals, the first surgical tool head adapted to be removably coupled to the robotic arm; and, (c) a second surgical tool head including a second electrical load in electrical communication with a second pair of electrical terminals, the second surgical tool head adapted to be removably coupled to the robotic arm, where the first pair of electrical terminals of the first surgical tool head are adapted to engage the first bipolar electrode and the second bipolar electrode to establish electrical communication between the first bipolar electrode and a first of the first pair of electrical terminals and between the second bipolar electrode and a second of the first pair of electrical terminals, and where the second pair of electrical terminals of the second surgical tool head are adapted to engage the first bipolar electrode and the second bipolar electrode to establish electrical communication between the first bipolar electrode and a first of the second pair of electrical terminals and between the second bipolar electrode and a second of the second pair of electrical terminals.

In a more detailed embodiment of the first aspect, the first and second jaws and the first pair of electrical terminals include complementarily engageable surfaces, and the complementary engageable surfaces include a protruding surface and a relieved surface, where the complementary engageable surfaces cooperate to enhance engagement between the first surgical tool head and the robotic arm. In yet another more detailed embodiment, the first and second jaws and the second pair of electrical terminals include complementarily engageable surfaces, and the complementary engageable surfaces include a protruding surface and a relieved surface, where the complementary engageable surfaces cooperate to enhance engagement between the second surgical tool head and the robotic arm. In a further detailed embodiment, the first and second jaws sandwich the first pair of electrical terminals therebetween when the robotic arm is coupled to the first surgical tool head, and the first and second jaws sandwich the second pair of electrical terminals therebetween when the robotic arm is coupled to the second surgical tool head. In still a further detailed embodiment, the first surgical tool head comprises at least one of a linear cutter, a cryosurgical probe, a clamp, an occlusion clip applicator, a dissector, an ablation and electrical signal detection device, and an ablation pen, and the second surgical tool head comprises at least one of a linear cutter, a cryosurgical probe, a clamp, an occlusion clip applicator, a dissector, an ablation and electrical signal detection device, and an ablation pen. In a more detailed embodiment, the robotic arm includes a first electric lead in electrical communication with the first bipolar electrode and a second electric lead in electrical communication with the second bipolar electrode. In a more detailed embodiment, the robotic arm includes a coupling adapted to receive a pair of electrical leads from an electric generator, and the coupling is individually connected to the first electric lead and the second electric lead.

It is a second aspect of the present invention to provide a surgical instrument kit comprising: (a) a robotic arm including a first bipolar electrode and a second bipolar electrode; (b) a first surgical tool head including a first electrical load in electrical communication with a first pair of electrical terminals, the first surgical tool head adapted to be removably coupled to the robotic arm; and, (c) a second surgical tool head including a second electrical load in electrical communication with a second pair of electrical terminals, the second surgical tool head adapted to be removably coupled to the robotic arm, where the first pair of electrical terminals of the first surgical tool head are adapted to engage the first bipolar electrode and the second bipolar electrode to establish electrical communication between the first bipolar electrode and a first of the first pair of electrical terminals and between the second bipolar electrode and a second of the first pair of electrical terminals, and where the second pair of electrical terminals of the second surgical tool head are adapted to engage the first bipolar electrode and the second bipolar electrode to establish electrical communication between the first bipolar electrode and a first of the second pair of electrical terminals and between the second bipolar electrode and a second of the second pair of electrical terminals.

In yet another more detailed embodiment of the second aspect, the robotic arm and the first pair of electrical terminals include complementarily engageable surfaces, and the complementary engageable surfaces include a protruding surface and a relieved surface, where the complementary engageable surfaces cooperate to enhance engagement between the first surgical tool head and the robotic arm. In still another more detailed embodiment, the robotic arm and the second pair of electrical terminals include complementarily engageable surfaces, and the complementary engageable surfaces include a protruding surface and a relieved surface, where the complementary engageable surfaces cooperate to enhance engagement between the second surgical tool head and the robotic arm. In a further detailed embodiment, the robotic arm includes a first electric lead in electrical communication with the first bipolar electrode and a second electric lead in electrical communication with the second bipolar electrode. In still a further detailed embodiment, the robotic arm includes a coupling adapted to receive a pair of electrical leads from an electric generator, and the coupling is individually connected to the first electric lead and the second electric lead. In a more detailed embodiment, the first surgical tool head comprises at least one of a linear cutter, a cryosurgical probe, a clamp, an occlusion clip applicator, a dissector, an ablation and electrical signal detection device, and an ablation pen, and the second surgical tool head comprises at least one of a linear cutter, a cryosurgical probe, a clamp, an occlusion clip applicator, a dissector, an ablation and electrical signal detection device, and an ablation pen.

It is a third aspect of the present invention to provide a method of providing power to a surgical instrument, the method comprising: (a) coupling a first robotic arm to a removable surgical tool head, the separable surgical tool head having at least two electrical terminals to receive electric current, and the first robotic arm including at least two electrical contacts; and (b) supplying electric current to the separable surgical tool head via the first robotic arm after coupling the first robotic arm to the separable surgical tool head, where the coupling step includes establishing electrical communication between the at least two electrical contacts of the first robotic arm and the at least two electrical terminals of the removable surgical tool head by making physical contact between the at least two electrical contacts of the first robotic arm and the at least two electrical terminals of the removable surgical tool head.

In yet another more detailed embodiment of the third aspect, the method further includes repositioning the removable surgical tool head using the first robotic arm after coupling the first robotic arm to the removable surgical tool head, and actuating an electrically driven mechanism associated with the removable surgical tool head using the electric current supplied from the first robotic arm. In still another more detailed embodiment, the electrically driven mechanism comprises at least one of a linear cutter, a clamp, a clip applicator, a cautery, and an electric motor.

It is a fourth aspect of the present invention to provide a surgical instrument kit comprising: (a) a first surgical tool head including a first electrical load in electrical communication with a first pair of electrical terminals that are spaced apart from one another, the first surgical tool head adapted to be removably coupled to a robotic arm, wherein the first surgical tool head comprises at least one of a linear cutter, a cryosurgical probe, a clamp, an occlusion clip applicator, a dissector, an ablation and electrical signal detection device, and an ablation pen; and, (b) a second surgical tool head including a second electrical load in electrical communication with a second pair of electrical terminals that are spaced apart from one another, the second surgical tool head adapted to be removably coupled to the robotic arm, wherein the second surgical tool head comprises at least one of a linear cutter, a cryosurgical probe, a clamp, an occlusion clip applicator, a dissector, an ablation and electrical signal detection device, and an ablation pen.

It is a fifth aspect of the present invention to provide a surgical instrument comprising: (a) a tool head; (b) a tether attached to the tool head for actuating the tool head; and, (c) at least one engagement surface adapted to interface with a separate control arm.

In yet another more detailed embodiment of the fifth aspect, the tool head is selected from the group consisting of an RF ablation clamp, an RF ablation pen, a blunt dissector and a clip applicator.

It is a sixth aspect of the present invention to provide a robotic surgical instrument comprising: (a) a first jaw including a first bipolar electrical lead; (b) a second jaw including a second bipolar electrical lead; (c) a robotic arm operatively coupled to the first jaw and the second jaw, the robotic arm including a coupling mounted to the first and second jaws that allows the first jaw to be repositioned with respect to the second jaw; and, (d) a surgical tool head including a first electrical load in electrical communication with a first and second electrical terminals, the first surgical tool head adapted to be mounted to the first and second jaws to establish a first junction between the first bipolar electrical lead and the first electrical terminal and a second junction between the second bipolar electrical lead and the second electrical terminal.

In yet another more detailed embodiment of the sixth aspect, the robotic surgical instrument further includes a housing mounted to the robotic arm so that the robotic arm is rotationally repositionable with respect to the housing, the housing at least partially enclosing a motor that is operatively coupled to the robotic arm to facilitate rotation of the robotic arm with respect to the housing. In still another more detailed embodiment, the surgical tool head comprises at least one of a linear cutter, a cryosurgical probe, a clamp, an occlusion clip applicator, a dissector, an ablation and electrical signal detection device, and an ablation pen.

BRIEF DESCRIPTION OF THE DRAWINGS

FIG. 23 is an overhead view of the exemplary magnetic, bipolar ablation clamp of FIG. 17, in the open position.

FIG. 24 is an elevated perspective view of the exemplary magnetic, bipolar ablation clamp of FIG. 17 in the open position.

FIG. 25 is a profile view of the exemplary magnetic, bipolar ablation clamp of FIG. 17 in the open position.

FIG. 26 is an end view of the exemplary magnetic, bipolar ablation clamp of FIG. 17 in the open position.

DETAILED DESCRIPTION

The exemplary embodiments of the present disclosure are described and illustrated below to encompass surgical instruments and, more specifically but not exclusively, robotic surgical instruments and methods for their use, which may comprise all or a portion of a robotic toolkit. Of course, it will be apparent to those of ordinary skill in the art that the embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure. Hereinafter, exemplary embodiments of the present disclosure will be described with reference to the drawings.

Figure 1:
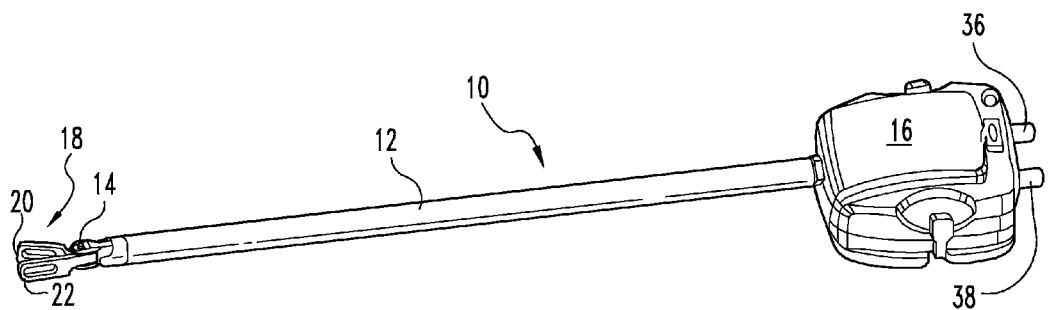
FIG. 1 is an elevated perspective view of an exemplary robotic arm.

With reference to FIG. 1, an exemplary robotic control arm 10 is a component of a telesurgical system (not shown). Exemplary telesurgical systems include those such as the daVinci® Surgical System, available from Intuitive Surgical, Inc. of Mountain View, Calif., disclosed in U.S. Pat. No. 6,770,081, the disclosure of which is incorporated herein by reference. The robotic control arm 10 includes an elongated shaft 12 and an axial adjustment coupling 14. A housing 16 at the proximal end of the shaft 12 couples the control arm 10 to the telesurgical system. The housing 16 contains the mechanism for controlling (e.g., rotating) the shaft 12, articulating the coupling 14, and actuating forceps 18 mounted to the coupling 14.

Figure 2A:
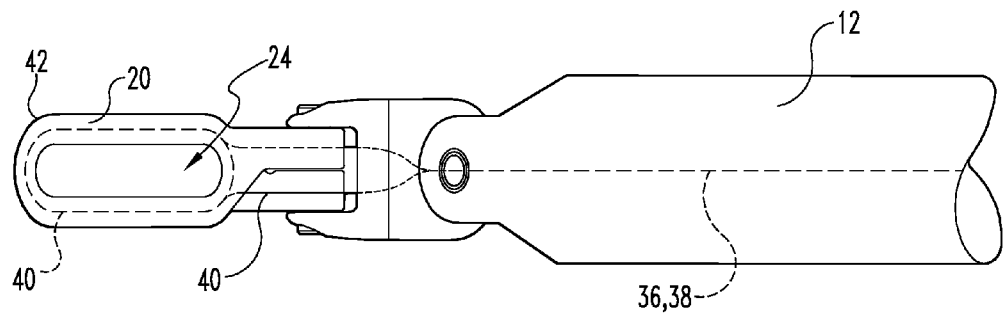
FIG. 2A is a profile view of the distal end of the exemplary robotic arm of FIG. 1.
Figure 2B:
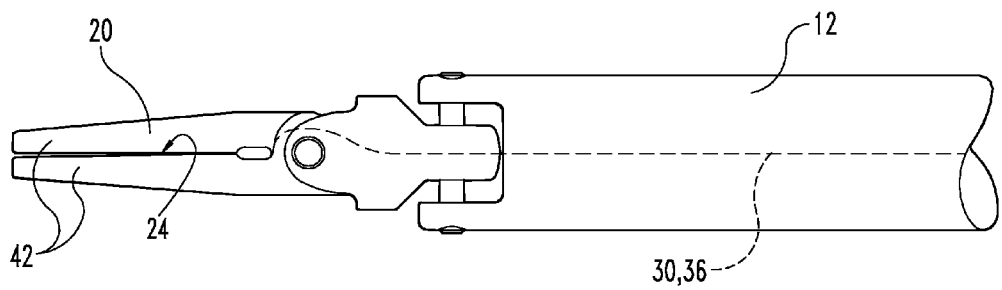
FIG. 2B is a profile view of the distal end of the exemplary robotic arm of FIG. 1.
Figure 3:
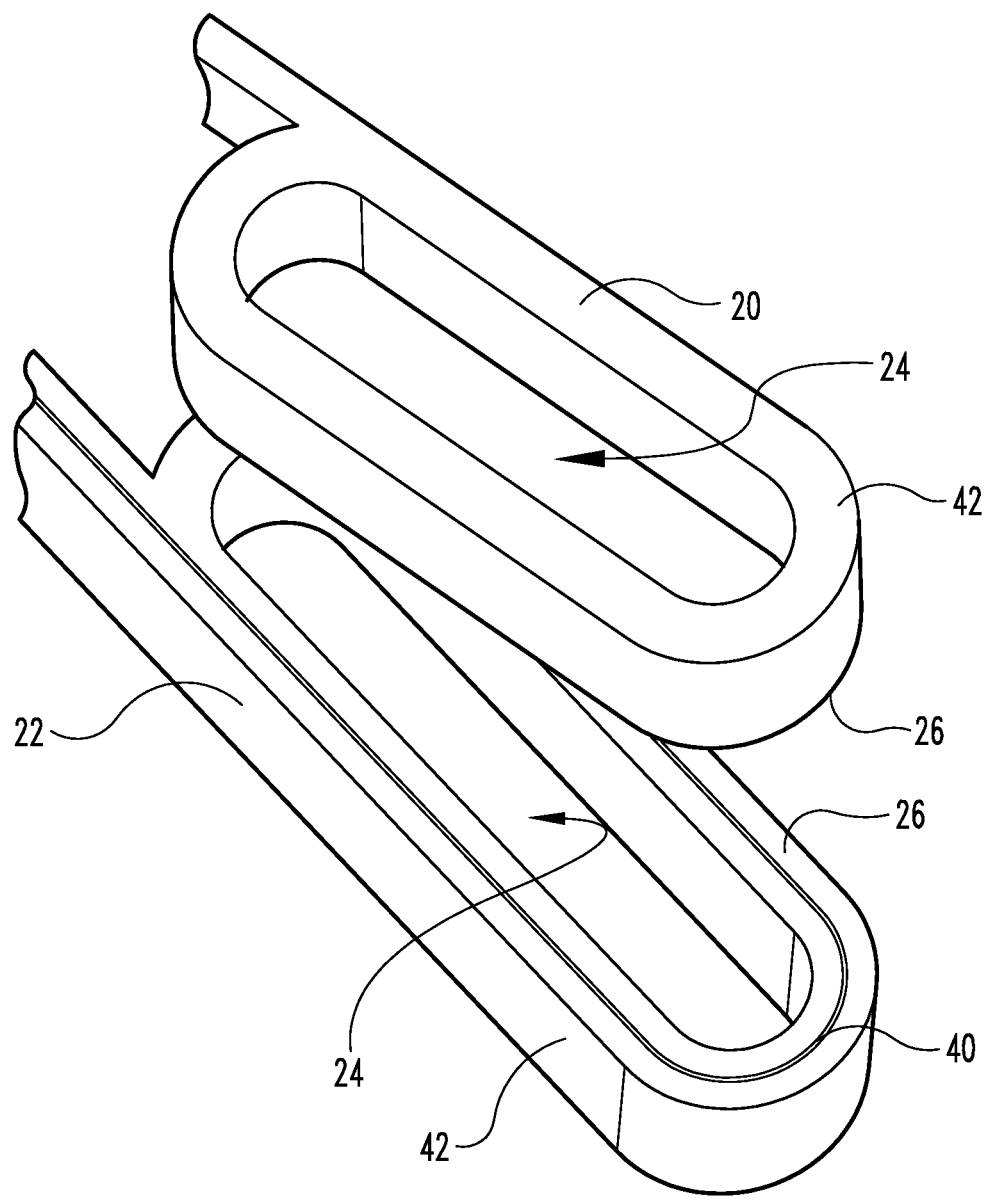
FIG. 3 is an elevated perspective view of the distal end of the robotic jaws of FIG. 1.

Referring to FIGS. 1-3, the forceps 18 include a first jaw 20, a second jaw 22. The exemplary forceps 18 is known as cardiere forceps in which each jaws 20, 22 is fenestrated. Specifically, each jaw 20, 22 is generally rectangular in shape, with rounded corners, and defines an oval opening 24. As will be discussed in more detail hereafter, this opening 24 is adapted to engage with a projection to facilitate mounting the robotic arm 10 to an interchangeable surgical tool. To further facilitate mounting the robotic arm 10 to one of the surgical tools, an inner surface 26 of each jaw 20, 22 may be serrated or smooth. In exemplary form, the jaws 20, 22 are repositionable anywhere between a fully open position and a closed position by movement of the mechanism located within the housing 16. More specifically, either or both of the jaws 20, 22 can be independently repositioned relative to one another.

The robotic control arm 10 is operative to deliver electrical current an interchangeable surgical tool (see FIGS.

1-30, Appendices I & II), having an associated electrical load, when mounted to the robotic control arm 10. In order to provide electrical current to the surgical tool, the jaws 20, 22 comprise an electrode 40 mounted to an insulative supporting frame 42. Each electrode 40 is fabricated from an electrically conductive material, such as, without limitation, stainless steel, platinum, nickel, or aluminum. Direct current is transmitted from an electrosurgical generator (now shown) via the wire leads 36, 38 to the electrodes 40. In this manner, the electric current is operative to flow between the jaws 20, 22 when current is supplied by the electrosurgical generator and the jaws are in electrical communication with one another, such as by interposing an electrical lead and electrical load.

Because the power source for each surgical tool is integrated into (i.e., supplied via or through) the control arm 10, various surgical tools may be used and exchanged for other surgical tools in an interchangeable manner. By way of example, this provides flexibility in having one robotic arm and various separable surgical tools that are utilized to carry out specific tasks, one at a time. This flexibility and redundancy in utilizing the same robotic arm 10 has particular benefit in a minimally invasive surgery procedure where, for example, the surgical tools to be used as part of the particular procedure may be inserted into the body cavity, creating what may be referred to as a toolkit or tool chest within the body cavity. In this manner, the surgeon or robotic instrument may use a single robotic arm 10 for grasping and using each surgical tool, as needed, without the need for repeatedly removing the robotic arm to exchange or replace the surgical tools. Further, the surgical tools may be for one-time use only and disposable, whereas the control arm, and any associated articulation control mechanism, is reusable, if so desired.

Figure 4:
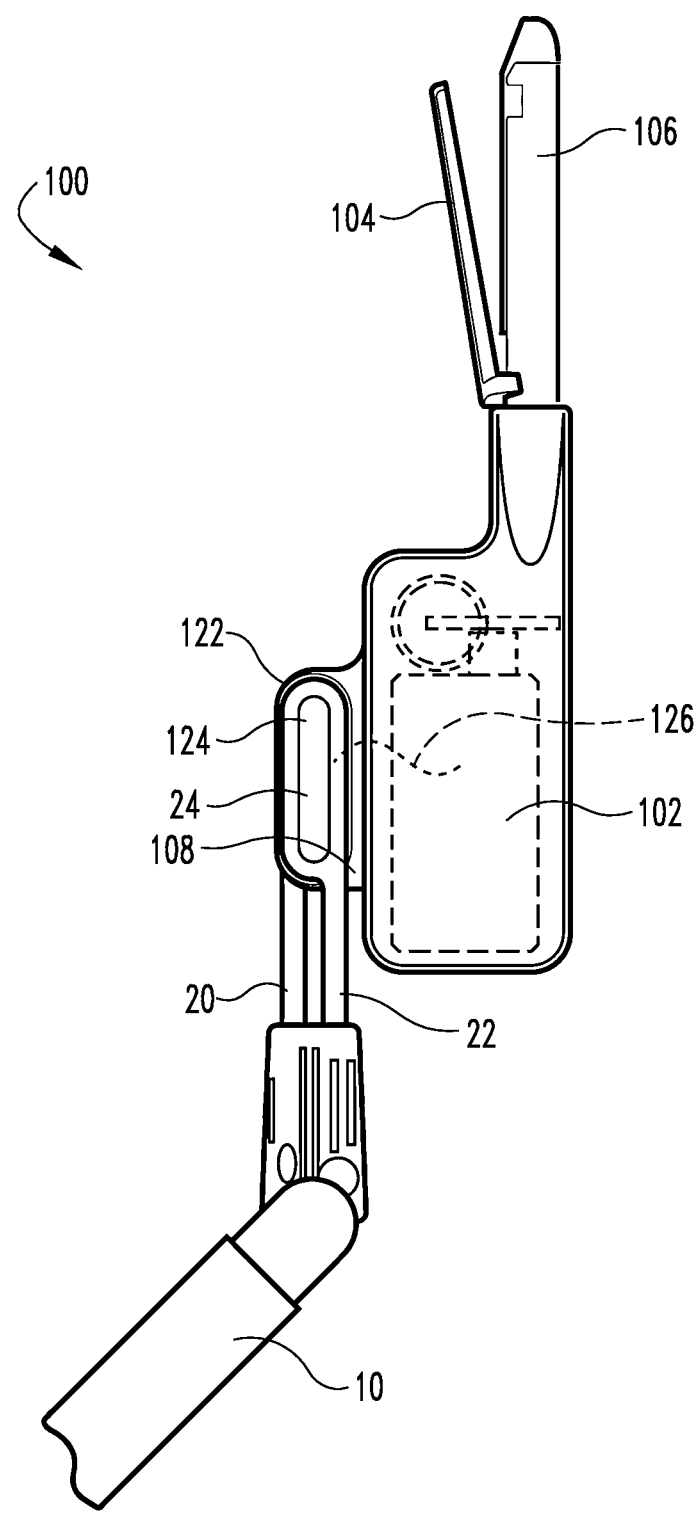
FIG. 4 is a profile view of an exemplary linear cutter in accordance with the instant disclosure, which is coupled to a robotic arm.

FIG. 4 illustrates an exemplary linear cutter 100 including a drive mechanism 102 and a pair of jaws 104, 106, at least one of which is pivotable relative to the other. In this exemplary embodiment, the bottom jaw 104 is repositionable, while the position of the top jaw 106 is fixed. These jaws 104, 106 are configured to staple and cut tissue placed therebetween generally in the manner described in U.S. Pat. No. 7,001,408, the disclosure of which is incorporated herein by reference.

In this exemplary embodiment, a robotic arm 10 includes a pair of jaws 20 that engage a clamping area 108 of the linear cutter 100 in order to couple the robotic arm 10 to the linear cutter 100. After the robotic arm is coupled to the linear cutter 100, a surgeon may use the robotic arm 10 to position the linear cutter 100 as desired. The clamping area 108 of the linear cutter 100 includes a lateral base 122 having a predetermined thickness from which oblong projections 124 extend from opposite sides. Surrounding each oblong projection 124 and mounted to the base 122 is an oblong pad 128 (underneath the jaw 22 in FIG. 4, for example), which is adapted to receive one of the jaws 20, 22 of the robotic arm 10. More specifically, each pad 128 (see FIG. 5) includes an electrical contact in electrical communication with the drive mechanism 102 by way of a lead 126. As was discussed in more detail previously, the jaws 20, 22 of the robotic arm 10 operate as bipolar electrical contacts, which provide electric current to the drive mechanism 102 of the linear cutter. Consequently, when the robotic arm 10 is coupled to the linear cutter 100 so the electrical contact of each pad 128 contacts a respective jaw 20, 22, electrical communication between the external power source and the drive mechanism 102 may be established.

In order to establish electrical communication between the external power source and the drive mechanism 102, the jaws 20, 22 must be properly seated on the pads 128. To properly seat the jaws 20, 22 on the pads 128, the jaws 20, 22 are opened so that the oblong opening 24 of each jaw is aligned with and overlies one of the oblong projections 124 of the linear cutter 100. Thereafter, the jaws 20, 22 are moved toward one another so that the oblong projections 124 pierce the openings 24 of the jaws 20, 22, thereby orienting the jaws 20, 22 to circumscribe the projections. Continued repositioning of the jaws 20, 22 toward one another occurs until the jaws ultimately sandwich the base 122 therebetween in a compression fit and bring the jaws 20, 22 in communication with the electrical contacts of the pads 128. This meeting between the electrical contacts establishes electrical communication between the external power source and the drive mechanism 102. As a result, when electrical power is supplied by the electrical power source in order to energize the electrical contacts of the jaws 20, 22, electrical power is able to flow to the drive mechanism 102.

Figure 5:
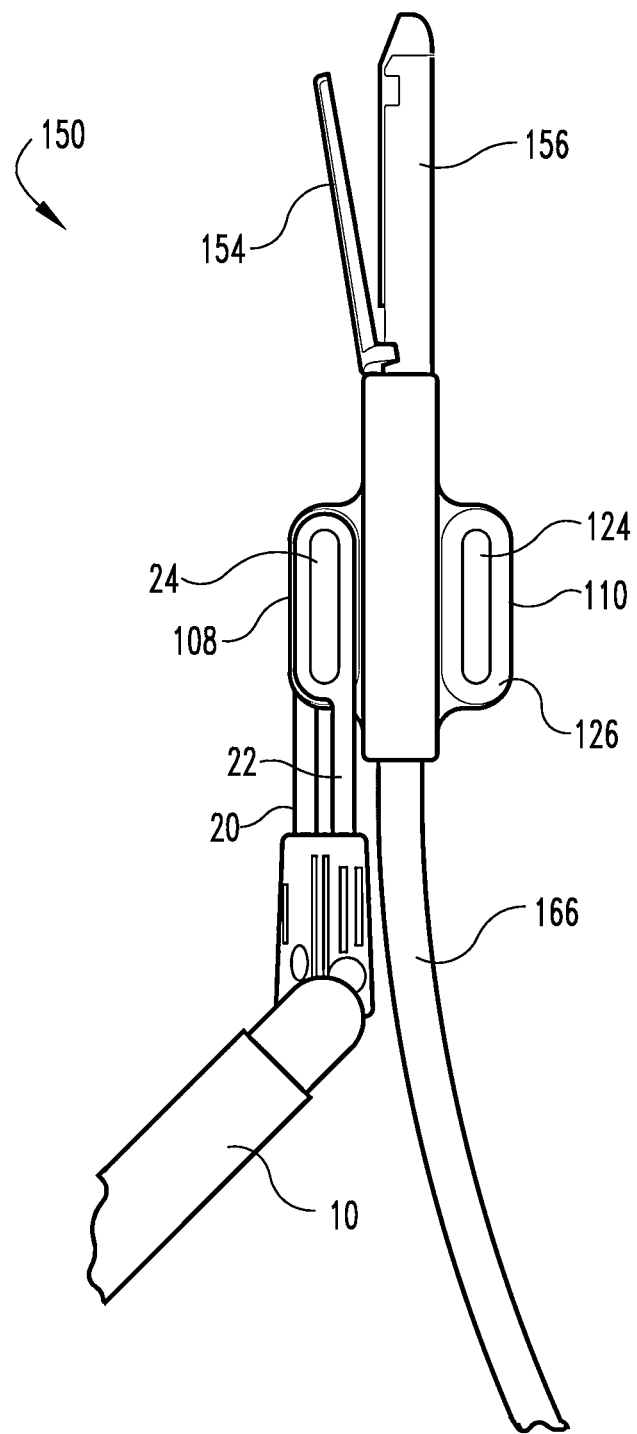
FIG. 5 is a profile view of another exemplary linear cutter in accordance with the instant disclosure, which is coupled to a robotic arm.

Referring to FIG. 5, an alternate exemplary linear cutter 150 including a drive mechanism 152 and a pair of jaws 154, 156, at least one of which is pivotable relative to the other. In this exemplary embodiment, the bottom jaw 154 is repositionable, while the position of the top jaw 156 is fixed. These jaws 154, 156 are configured to staple and cut tissue placed therebetween generally in the manner described in U.S. Pat. No. 7,001,408, the disclosure of which is incorporated herein by reference.

As with the foregoing exemplary embodiment, a robotic arm 10 includes a pair of jaws 20 that engage at least one of the clamping areas 108, 110 of the linear cutter 150 in order to couple the robotic arm 10 to the linear cutter 150. After the robotic arm 10 is coupled to the linear cutter 150, a surgeon may use the robotic arm 10 to position the linear cutter 100 as desired. Coupling the robotic arm 10 to the linear cutter 150 is generally the same as was described in the foregoing embodiment and has been omitted here only for purposes of brevity.

The exemplary linear cutter includes an external cable assembly 166 to drive and power the linear cutter in lieu of using the robotic arm 10. More specifically, the robotic arm 10 may be utilized to power the stapling functionality, while the cable assembly is operative to power the cutting functionality, or vice versa. In exemplary form, the cable assembly 166 includes at least one cable (not shown) disposed within a sheath. The cable is configured to rotate and/or translate within sheath in order to transfer mechanical energy from an external source (not shown) to the linear cutter drive mechanism, thereby actuating at least one of the stapling and/or cutting functions of linear cutter 150. While those skilled in the art will realize that a single cable of the cable assembly 166 is operative to actuate stapling and/or cutting functions of the linear cutter 150, it is also within the scope of the disclosure to utilized separate cables to effectuate mechanical and electrical functionality, including the stabling function and the cutting function.

Figure 6:
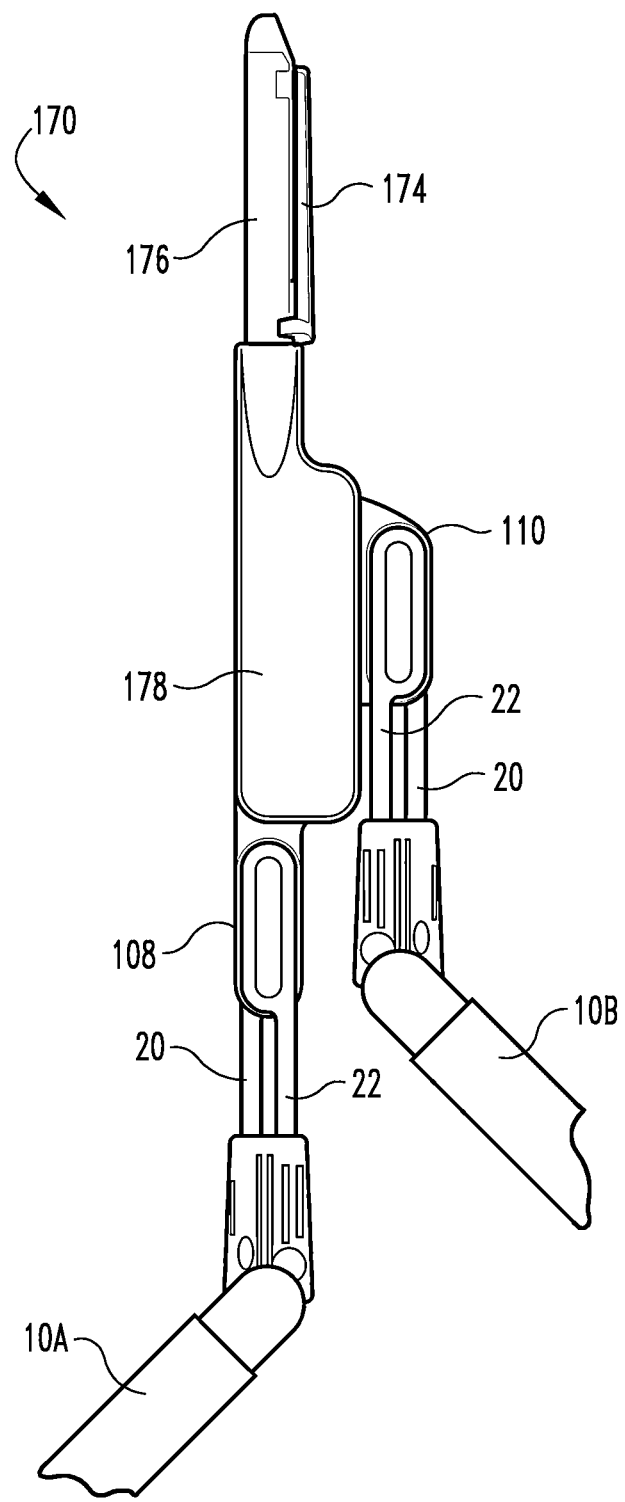
FIG. 6 is a profile view of a further exemplary linear cutter in accordance with the instant disclosure, which is coupled to two robotic arms.

With reference to FIG. 6, a further alternate exemplary linear cutter 170 including a manual drive mechanism 172 and a pair of jaws 174, 176, at least one of which is pivotable relative to the other. In this exemplary embodiment, the bottom jaw 174 is repositionable, while the position of the top jaw 176 is fixed. These jaws 174, 176 are configured to staple and cut tissue placed therebetween generally in the manner described in U.S. Pat. No. 7,001,408, the disclosure of which is incorporated herein by reference.

In this exemplary embodiment, the linear cutter 170 includes a pair of clamping areas 108, 110, with each clamping area being coupled to a separate robotic arm 10A, 10B. The first clamping area 108 is integral with the cutter housing 178, while the second clamping area 110 slidably engages the cutter housing. More specifically, the housing 178 includes an electric motor operatively coupled to the bottom jaw 174 and a stapling mechanism (not shown) operatively coupled to the second clamping area 110. The first robotic arm 10A provides electrical power sufficient to power a motor (not shown) operatively coupled to the bottom jaw 174. In exemplary form, the stapling action is carried out by repositioning the second robotic arm 10B rearward, toward the first robotic arm 10A, which causes the stapling mechanism to be repositioned, thereby causing the stapling action. However, those skilled in the art will realize, based upon the instant disclosure, that repositioning the second robotic arm 10B with respect to the first robotic arm 10A may control a variety of functions including cutting or a combination of cutting and stapling.

Figure 7:
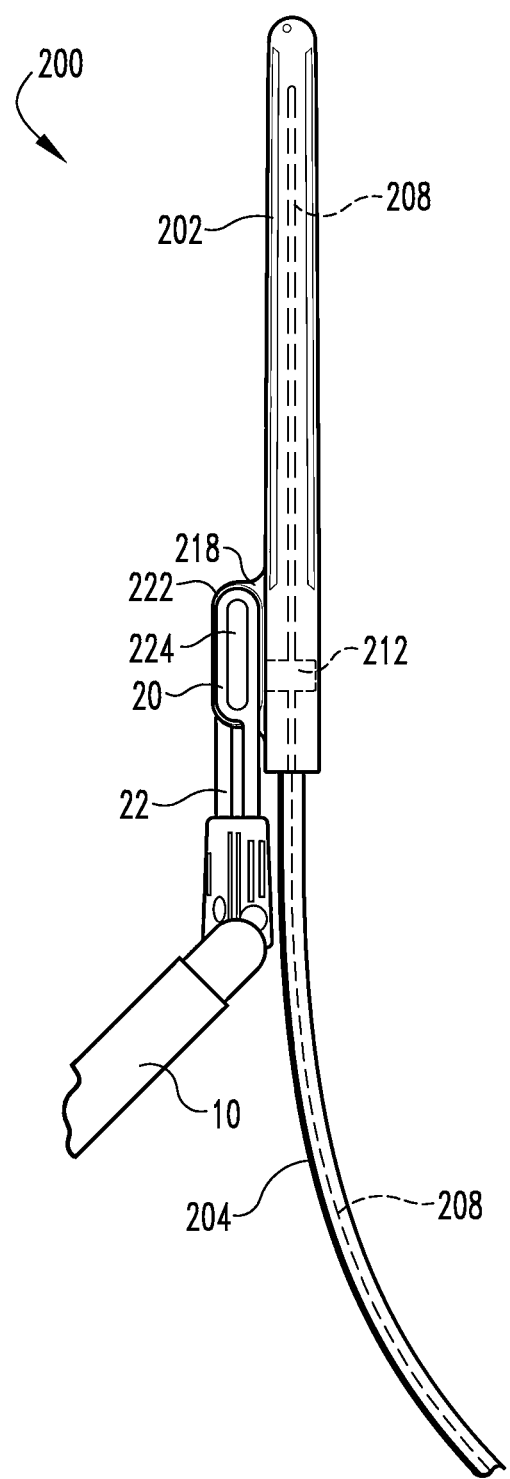
FIG. 7 is a profile view of an exemplary cryosurgical probe in accordance with the instant disclosure, which is coupled to a robotic arm.
Figure 8:
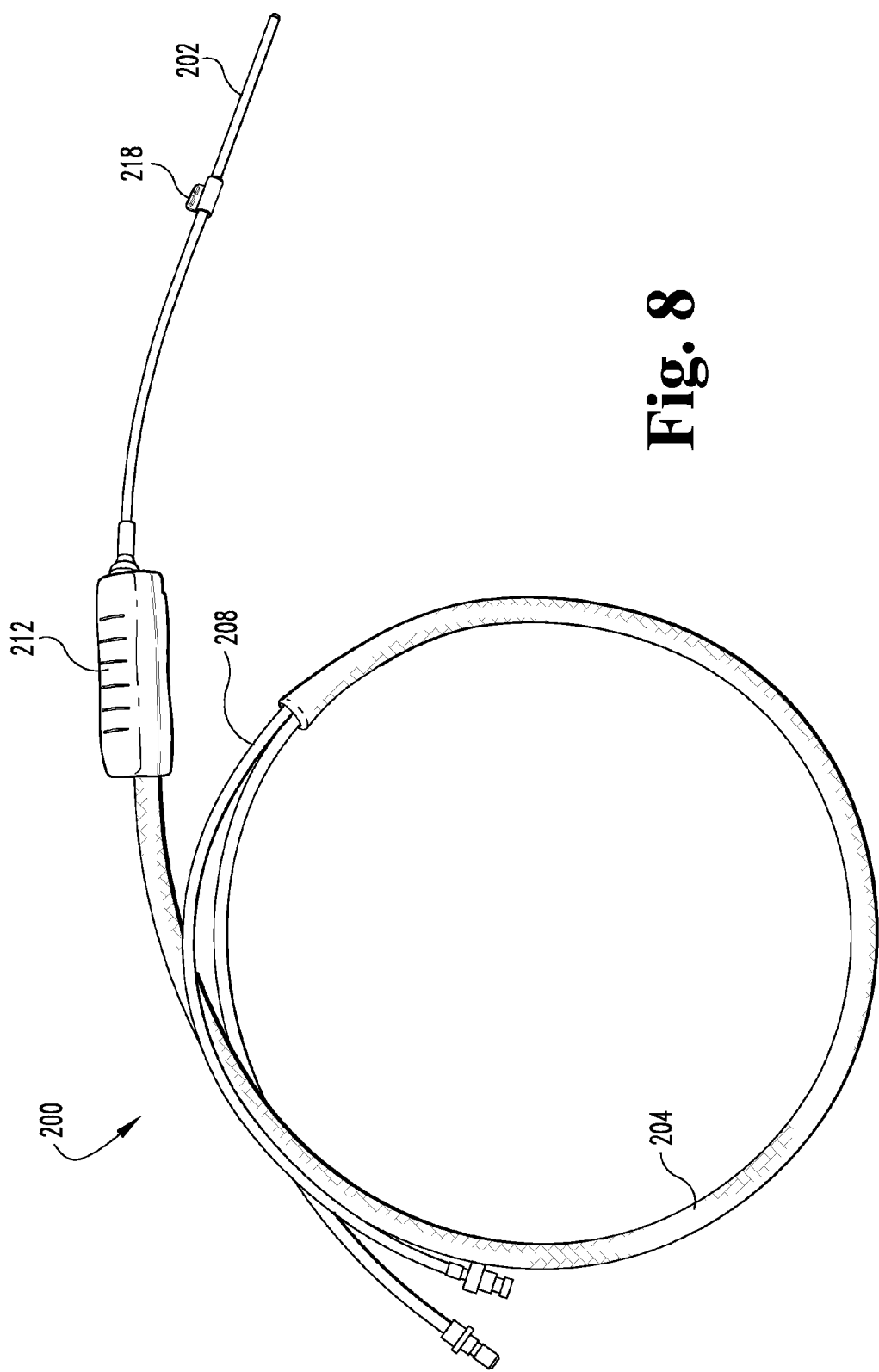
FIG. 8 is a photograph of the exemplary cryosurgical probe.

Referring to FIGS. 7 and 8, an exemplary cryosurgical probe 200 includes an ablation tube 202. The ablation tube 202 is selectively supplied with a cryogenic fluid (e.g., nitrous oxide, argon, etc.) via an umbilical line 204, which is also operative to withdraw spent cryogenic fluid from a distal end of the tube 202. The ablation tube 202 may be constructed generally as described in U.S. Pat. No. 3,993,075, the disclosure of which is incorporated by reference, as well as constructed in accordance with U.S. patent application Ser. No. 12/727,995, filed Mar. 19, 2010 and published as US 2010/0241114 on Sep. 23, 2010, the disclosures of which are incorporated herein by reference. Housed within the ablation tube 202 is a cryogenic fluid conduit 208 having one or more exit orifices (not shown) that are in communication with an interior of the tube. The cryogenic fluid conduit 208 also extends through the umbilical line 204 and is in fluid communication with an external cryogenic fluid source (not shown). An electrically actuated valve 212 may be placed in series with the cryogenic fluid conduit 208 that is operative to selectively allow cryogenic fluid flowing through the umbilical line 204 to reach the exit orifices. In order to manipulate the valve 212, electrical power is provided by the robotic arm 10.

The cryosurgical probe 200 includes a clamping area 218 having a lateral base 222 with a predetermined thickness from which oblong projections 224 extend from opposite sides. Surrounding each oblong projection 224 and mounted to the base 222 is an oblong pad, which is adapted to receive one of the jaws 20, 22 of the robotic arm 10. More specifically, each pad includes an electrical contact in electrical communication with the valve 212 by way of a lead. As was discussed in more detail previously, the jaws 20, 22 of the robotic arm 10 include bipolar electrical contacts in electrical communication with an external power source (not shown). Thus, when the robotic arm 10 is coupled to the cryosurgical probe 200 so the electrical contacts of the pads touch the jaws 20, 22, electrical communication between the external power source and the valve 212 may be established.

By way of example, the exemplary cryosurgical probe 200 may be used in surgical procedures including, without limitation, atrial tissue ablation to treat atrial fibrillation. After the robotic arm 10 is coupled to the cryosurgical probe 200, a surgeon may use the robotic arm 10 to position, orient, and/or move cryosurgical probe 200 as desired. More specifically, the separability of the cryosurgical probe 200 from the robotic arm 10 enables the robotic arm to be utilized with additional devices, such as the linear cutter 100 discussed above, without ever removing the robotic arm from the patient's body. This is particularly advantageous in minimally invasive procedures.

Alternatively, the cryosurgical probe may include the structure as disclosed in Appendix I, attached hereto and made part of the instant disclosure.

Figure 9:
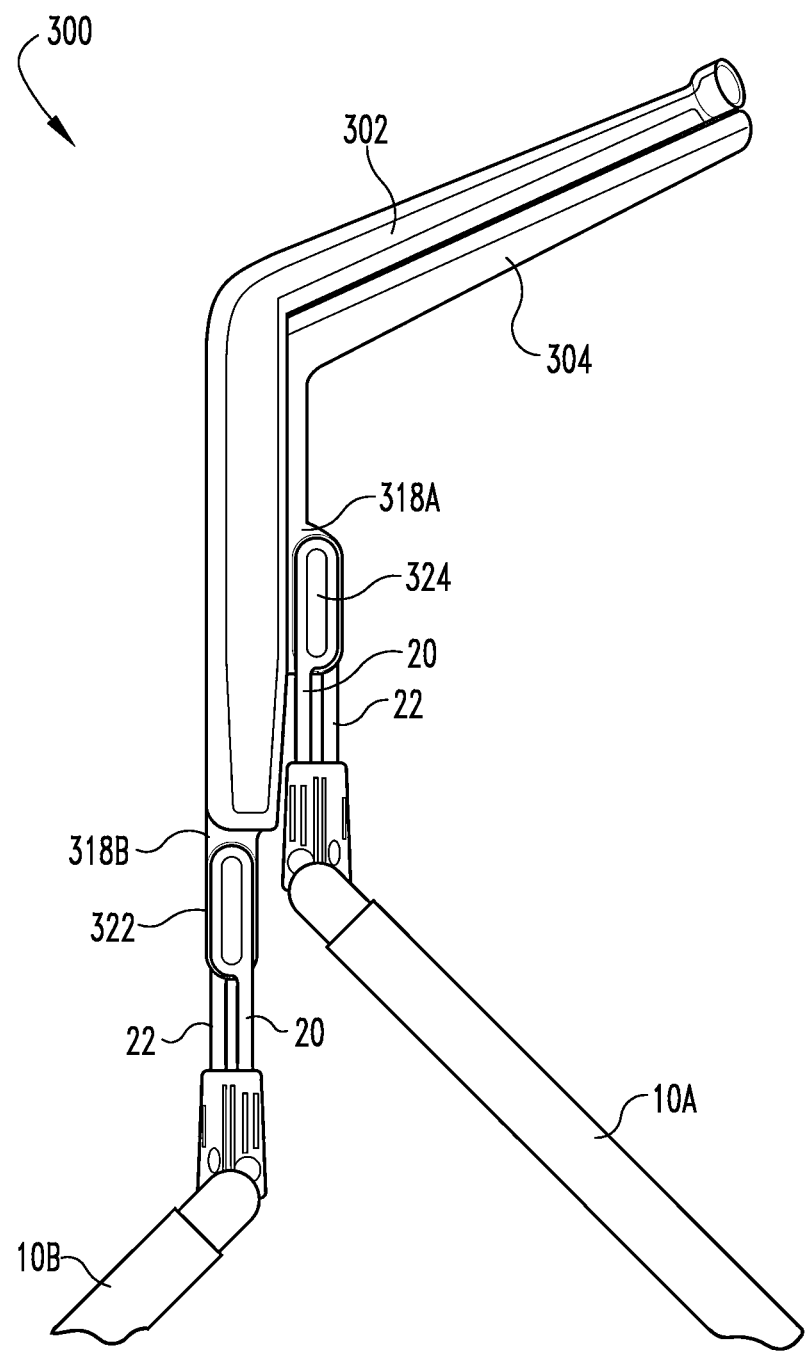
FIG. 9 is a profile view of an exemplary clamp in accordance with the instant disclosure, which is coupled to two robotic arms.

FIG. 9 illustrates an exemplary clamp 300 having opposed jaws 302, 304 for use with a pair of robotic arm assemblies 10A, 10B (see FIG. 1). The jaws 302, 304 are similar to those generally described in U.S. Pat. No. 6,923,806, the disclosure of which is incorporated herein by reference. The illustrated clamping jaws 302, 304 include an elongated electrode (not shown) that is adapted to receive bipolar RF energy for creating transmural ablation lines in tissue held between the jaws 302, 304. In this exemplary embodiment, the distal jaw 302 is considered to be stationary, while the proximal jaw 304 traverses longitudinally along a track (not shown) formed within the longitudinal portion of the distal jaw 302. However, based upon the fact that each of the jaws 302, 304 is coupled to a separate robotic arm 10A, 10B, each jaw is able to move independent of the other based upon relative movement of the robotic arms 10A, 10B with respect to one another.

In order to mount the robotic arms 10A, 10B to the clamp 300, each arm is initially aligned with its corresponding clamping area 318. Each of the jaws 302, 304 includes a clamping area 318A, 318B that comprises a base 322 with a predetermined thickness from which oblong projections 324 extend from opposite sides. In this exemplary embodiment, the clamping area 318B for the distal jaw 302 extends longitudinally from a proximal end of the longitudinal portion. Somewhat similarly, the clamping area 318A for the proximal jaw 304 extends proximally and laterally from a proximal end of the proximal jaw. This orientation of the clamping areas 318A, 318B allows the robotic arms 10A, 10B to individually couple to the jaws 302, 304, while preserving the necessary range of motion needed by the robotic arms to open and close the jaws their own jaws 20, 22.

In this exemplary embodiment, the electrical and mechanical connections for activating the electrodes carried on the jaws 302, 304 and for opening and closing the jaws are integrated into the robotic arms 10A, 10B. Surrounding each oblong projection 324 and mounted to the base 322 is an oblong pad, which is adapted to receive one of the jaws 20, 22 of a robotic arm 10A, 10B. More specifically, each pad includes an electrical contact in electrical communication, via an electrical lead (not shown), with the elongated electrode (not shown) that is adapted to receive bipolar RF energy for creating transmural ablation lines. As was discussed in more detail previously, both jaws 20, 22 of each robotic arm 10A, 10B include a bipolar electrical contact in electrical communication with an external power source (not shown) by way individual leads (see FIGS. 2A, 2B). Consequently, when a robotic arm 10A, 10B is coupled to a respective jaw 302, 304 so the electrical contact of a pad associated with the clamp touches the electrical contacts of the jaws 20, 22, electrical communication between the external power source and clamp electrodes (i.e., the electrical load) can be established.

Because the mechanical and electrical sources to reposition and power the clamp 300 are separate from the clamp, the clamp 300 may be released from the robotic arms 10A, 10B and a different surgical tool attached to the robotic arms. This separability and interchangeability allows a surgeon to select multiple surgical tools and position these tools at a preselected location in or near the surgical site for convenience during a surgical procedure, such as a minimally invasive surgical procedure. Simply put, the surgical tools are inserted into the body cavity, creating what may be referred to as a tool kit or tool chest within the body cavity, and the surgeon uses one or more robotic arms 1 OA, 10B to selectively couple, reposition, and power the surgical tool necessary to perform all or a portion of the surgical procedure without the need for repeatedly removing one or more of the robotic arms and/or surgical tools. Those skilled in the art will understand that the surgical tools (e.g., described above in exemplary form as a linear cutter 100, 150, 170, a cryosurgical probe 200, and a clamp 300) may be for one-time use only and disposable, with the robotic arms 10, 10A, 10B being reusable, if so desired.

Figure 10:
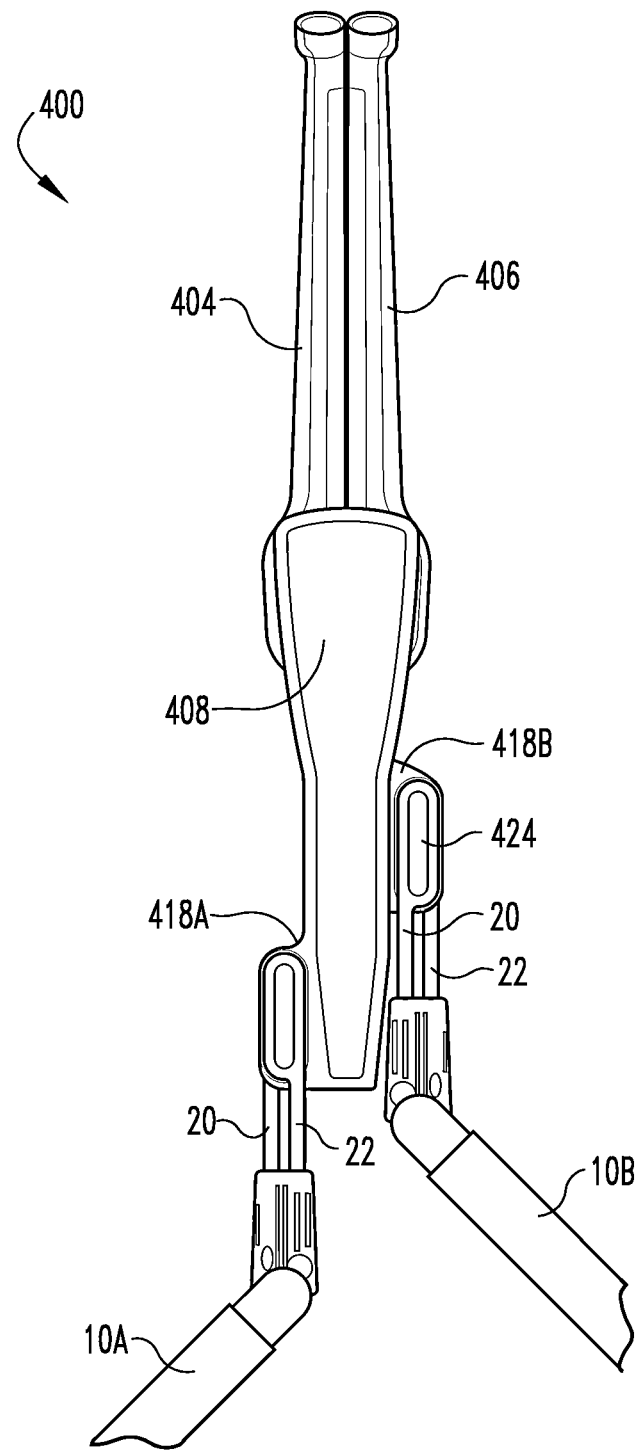
FIG. 10 is a profile view of another exemplary clamp in accordance with the instant disclosure, which is coupled to two robotic arms.

FIG. 10 illustrates an exemplary in-line clamp 400, which may be fabricated in accordance with the disclosure of U.S. patent application Ser. No. 12/748,842, entitled "SURGICAL CLAMP," the disclosure of which is incorporated herein by reference. This exemplary in-line clamp 400 includes a pair of jaws 404, 406, that open and close in two stages. Starting from a closed position, the jaws 404, 406 are progressively apart from one another, but maintain a generally parallel configuration. At a predetermined point, the jaws 404, 406 flare out from one another and discontinue a parallel configuration. As the jaws 404, 406 are opened to a maximum, the distal ends of the jaws are the portions farthest apart from one another, while the proximal ends are spaced apart from one another, but significantly closer than are the distal ends.

This exemplary in-line clamp 400 includes two robotic arm clamping areas 418A, 418B, each being on an opposite side of the clamp housing 408. Similar to the embodiments discussed previously, each clamping area 418A, 418B includes a base with a predetermined thickness from which oblong projections 424 extend from opposite sides. Because the clamping areas 418A, 418B are on opposite sides of the housing 408, separate robotic arms 10A, 10B may be coupled to the clamp by way of the clamping areas. Moreover, this orientation of the clamping areas 418A, 418B also preserves a range of motion for each robotic arm 10A, 10B, which is useful to open and close the jaws 404, 406. In this exemplary embodiment, the first clamping area 418A is fixedly mounted to the clamp housing 408 and to the first robotic arm 10A, whereas the second clamping area 418B is part of a carriage that is repositionably mounted to the clamp housing 408. As a result, the robotic arms 10A, 10B are repositionable with respect to one another even when mounted to respective clamping areas 418A, 418B.

Articulation of jaws 404, 406 (e.g., from an open position to a closed position) may be effectuated by moving one of the robotic arms 10A with respect to the other robotic arm 10B. Those skilled in the art will realize that which robotic arm 10A, 10B is moved, if only one, is not as important as the relative motion between the robotic arms. By way of exemplary explanation, in order to open the jaws 404, 406 from the closed position shown in FIG. 10, to a variant of an open position, the first robotic arm 10A is kept stationary, while the second robotic arm 10B is repositioned proximally, away from the jaws 404, 406.

Alternatively, the jaws 404, 406 may be repositioned using an electric motor (not shown). In this circumstance, the electric motor is located within the in-line clamp housing 408. The electric motor is operatively coupled to the jaws 404, 406 by way of a repositioning mechanism. This repositioning mechanism may comprise any combination of gears, pulleys, and cord to convert the motion of the electric motor into motion of the jaws 404, 406. For example, the electric motor is operatively coupled to one or more gears, which are coupled to a rack (see rack 832 from U.S. patent application Ser. No. 12/748,842) in order to reposition the rack with respect to gears directly mounted to the jaws 404, 406. The electric motor may be powered by either robotic arm 10A, 10B based upon the electrical communication established between the robotic arms and the clamping areas 418A, 418B.

Figure 11:
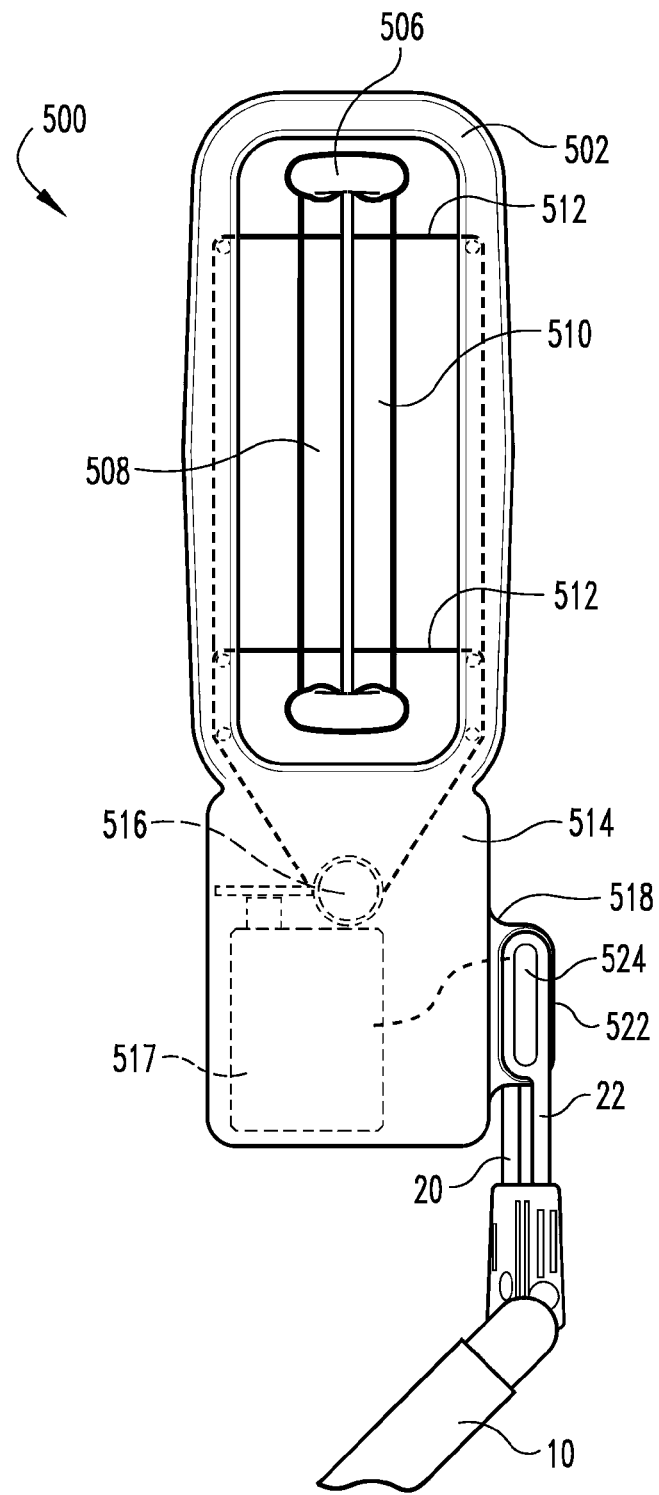
FIG. 11 is a profile view of an exemplary clip applicator in accordance with the instant disclosure, which is coupled to a robotic arm.
Figure 12:
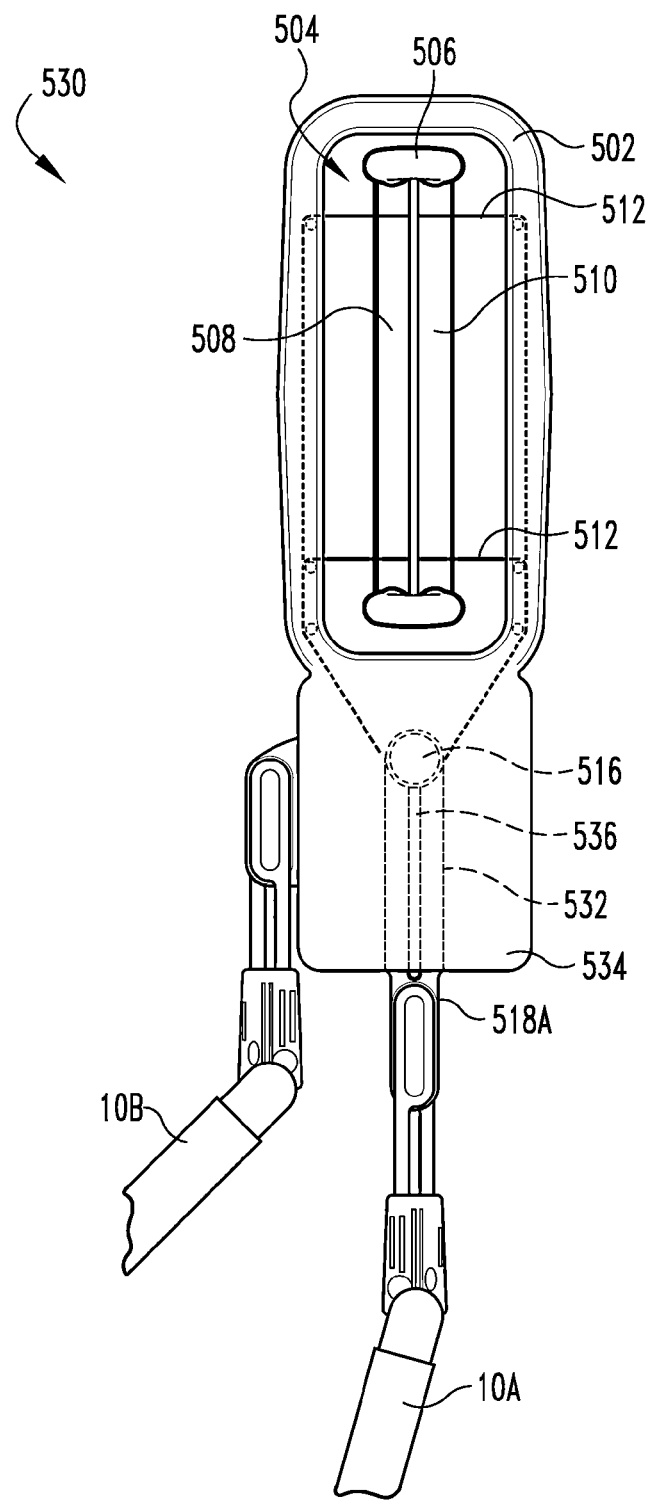
FIG. 12 is a profile view of another exemplary clip applicator in accordance with the instant disclosure, which is coupled to two robotic arms.

FIG. 11 illustrates an exemplary clip applicator 500 being coupled to a robotic arm 10. The clip applicator 500 includes a rounded rectangular frame 502 that defines a working area 504. Within the working area 504 is an occlusion clip 506 mounted to the rectangular frame 502 using two sutures 512. The clip 506 includes an upper jaw 508 and a lower jaw 510 that are biased in the closed position, as shown in FIG. 11. In order to overcome the bias of the clip jaws 508, 510, a first end of each suture 512 is wound around a respective clip jaw and threaded along the rectangular frame 502 to extend into an applicator housing 514, where a second end of each suture is wound around a spool 516. Also within the applicator housing 514 is an electric motor 517 operatively coupled to the spool 516 in order to rotate the spool and wind additional suture on the spool or unwind suture from the spool. By winding additional suture 512 on the spool 516, the clip jaws 508, 510 are pulled apart so that a patient's tissue may be repositioned to interposes the jaws, after which time the spool is unwound or the sutures are severed to clamp the tissue between the jaws 508, 510.

In order to turn the spool 516 and manipulate the sutures 512, electric power is supplied via the bipolar jaws 20, 22 of the robotic arm 10. In this exemplary embodiment, similar to the foregoing exemplary embodiments, the clip applicator 500 includes clamping areas 518. Each clamping area 518 shares a base 522 with a predetermined thickness from which oblong projections 524 extend from opposite sides. The clamping areas 418 extends from a proximal side of the applicator housing 514.

Referencing FIG. 11, an alternate exemplary clip applicator 530 does not include an electric motor, but does include several of the aforementioned features/elements from the previous clip applicator 500. In this alternate exemplary embodiment, the spool 516 is locked so that no further rotational motion is permitted. However, the spool 516 is longitudinally repositionable along a track 532 formed into the applicator housing 534. In order to reposition the spool 516 toward the proximal end of the applicator housing 534 (away from the clip 506), the clamping area 518A for the second robotic arm 10A is repositionably mounted to the applicator housing. The clamping area 518A includes an appendage 536 that extends into the applicator housing 534 and is operatively coupled to the spool 516. Optionally, this appendage 436 is repositionable along the track 532 so that longitudinal motion of the appendage is operative to longitudinally reposition the spool 516 a corresponding distance.

In operation, in order to overcome the bias of the clip jaws 508, 510, the spool 516 is longitudinally repositioned toward the proximal end of the applicator housing 534. This movement of the spool 516 correspondingly causes the sutures 512 to become tensioned to a sufficient degree to overcome the bias of the clip jaws 508, 510, thereby causing the sutures to effectively pull apart the clip jaws. In order to longitudinally reposition the spool 516, the first robotic arm 10B is maintained in a first position, which is operative to maintain the applicator housing 534 in the same first position, while the second robotic arm 10A is repositioned proximally with respect to the first position, thereby moving the second robotic arm 10A, the appendage 536, and the spool 516 proximally. The net movement between the first robotic arm 10B and the second robotic arm 10A causes the spool 516 to be repositioned along the track 532. After the clip jaws 508, 510 are appropriately positioned so that the patient's tissue to be clamped is between the jaws, the sutures are severed or the robotic arms 10A, 10B are relatively repositioned to cause the spool 516 to move distally so the sutures are no longer operative to retard the jaws from clamping toward one another.

Alternatively, the clip applicator may include the structure as disclosed in Appendix II, attached hereto and made part of the instant disclosure.

Figure 13:
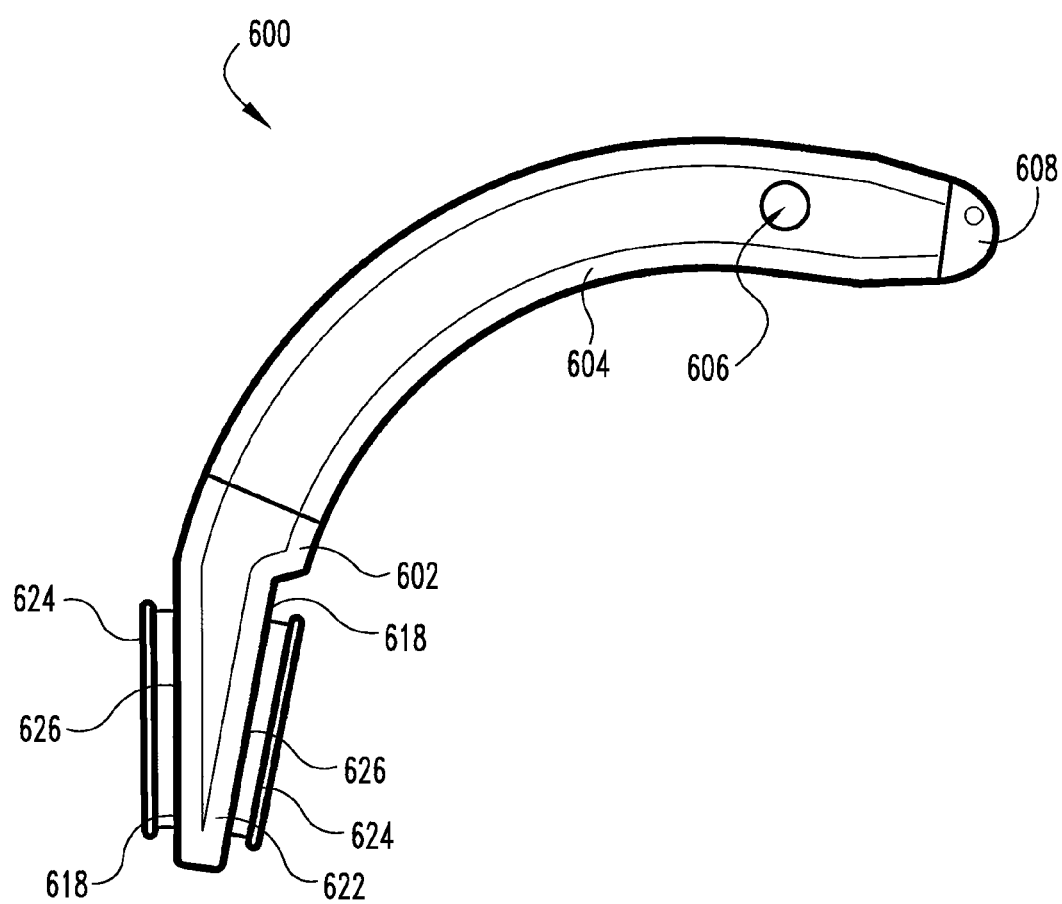
FIG. 13 is a profile view of an exemplary illuminated dissector in accordance with the instant disclosure.

FIG. 13 illustrates an exemplary illuminated dissector 600, which may be generally similar to the dissectors described in U.S. Patent Application Publication No. 2005/0203561 (U.S. patent application Ser. No. 10/796,901), the disclosure of which is incorporated herein by reference. This exemplary dissector 600 includes clamping areas 618 on a support 602 from which extends a flexible appendage 604. The flexible appendage 604 includes a suture hole 606 and a light emitting diode (LED) 608 at its distal tip. In order to provide electric current to the LED 608, electrical leads (not shown) extend from the LED and into electrical communication with the electrical contacts of the pads 626 of the clamping areas 618. The clamping areas 618 are similar in structure to the clamping areas described in the foregoing embodiments and, for purposes of brevity, a detailed explanation of the structure of these clamping areas 618 has been omitted.

Repositioning of the dissector 600 and illumination of the LED 608 are both controlled by a robotic arm (not shown) mounted thereto. Consistent with the foregoing embodiments (see FIGS. 1-3), the jaws 20, 22 of the robotic arm 10 must be properly seated on the pads 626. To do this, the jaws 20, 22 are opened so that the oblong opening 24 of each jaw is aligned with and overlies one of the oblong projections 624 of the dissector 600. Thereafter, the jaws 20, 22 are moved toward one another so that the oblong projections 624 pierce the openings 24 of the jaws 20, 22, thereby orienting the jaws 20, 22 to circumscribe the projections and ultimately sandwich the base 622 therebetween in a compression fit. This compression fit also establishes electrical communication between the contacts of the jaws 20, 22 and the contacts of the pads 626, which ultimately establishes electrical communication between the LED 608 and an external power source (not shown). As a result, when electrical power is supplied by the electrical power source, illumination at the distal tip of the dissector 600 occurs via the LED 608.

Figure 14:
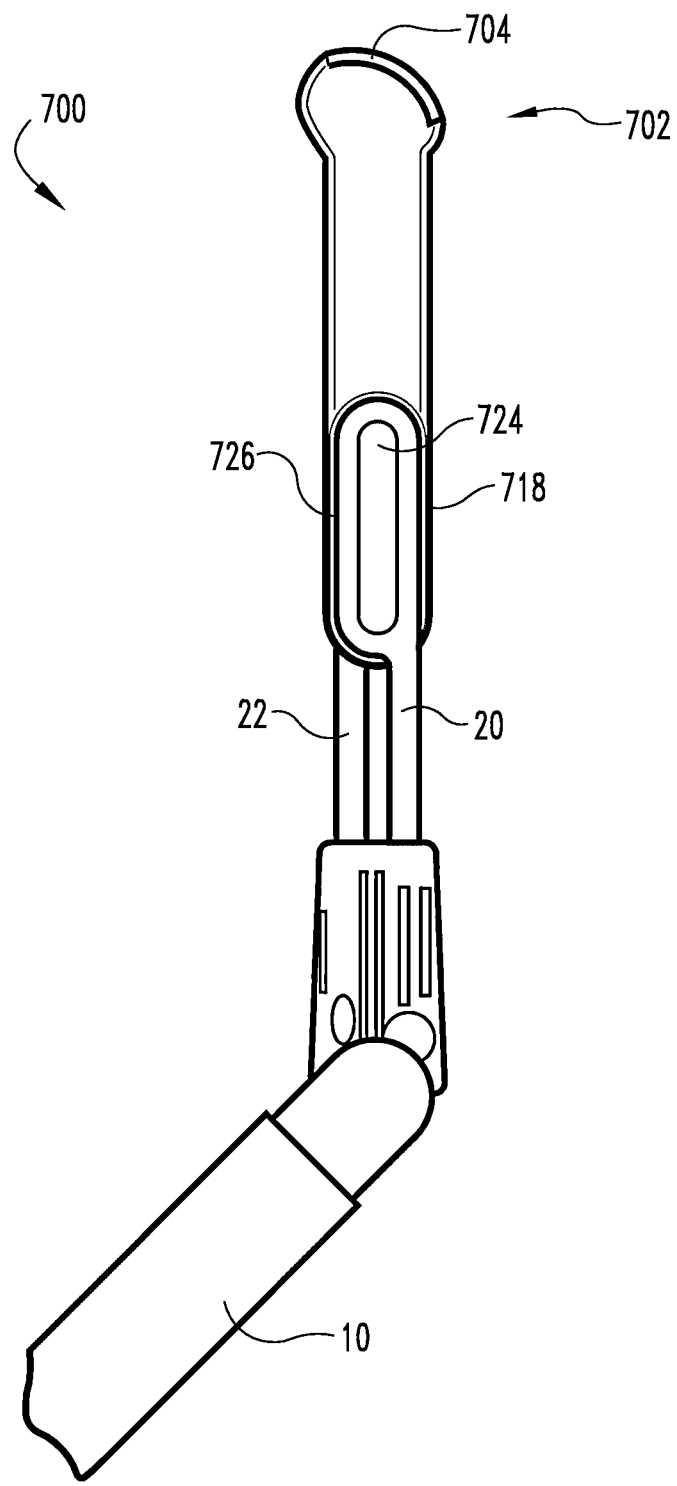
FIG. 14 is a profile view of an exemplary ablation pen in accordance with the instant disclosure, which is coupled to a robotic arm.

FIG. 14 illustrates an exemplary ablation pen 700, having a distal portion 702 generally similar to the ablation device disclosed in U.S. Patent Application Publication No. 2008/0009853 (U.S. patent application Ser. No. 11/457,919), the disclosure of which is incorporated herein by reference. The ablation pen 700 includes clamping areas 718 similar those to the clamping areas disclosed in the foregoing exemplary embodiments. To further brevity, a detailed discussion of the structure of the clamping areas 718 has been omitted. The distal portion 702 includes an ablation electrode 704 that is in electrical communication with the robotic jaws 20, 22 by way of an electric lead (not shown) extending between the clamping area 718 and the electrode.

Repositioning of the ablation pen 700 and energizing the ablation electrode 704 are both controlled by the robotic arm 10 mounted thereto. Consistent with the foregoing embodiments, the jaws 20, 22 of the robotic arm 10 must be properly seated on the pads 726. To do this, the jaws 20, 22 are opened so that the oblong opening 24 of each jaw is aligned with and overlies one of the oblong projections 724 of the ablation pen 700. Thereafter, the jaws 20, 22 are moved toward one another so that the oblong projections 724 pierce the openings 24 of the jaws 20, 22, thereby orienting the jaws 20, 22 to circumscribe the projections and ultimately sandwich the clamping area 818 therebetween in a compression fit. This compression fit also establishes electrical communication between the contacts 40 of the jaws 20, 22 and the contacts of the pads 726, which ultimately establishes electrical communication between the ablation electrode 804 and an external power source (not shown). As a result, when electrical power is supplied by the electrical power source, energizing of the ablation electrode 704 at the distal tip of the ablation pen 700 occurs.

Figures 15A, 15B:
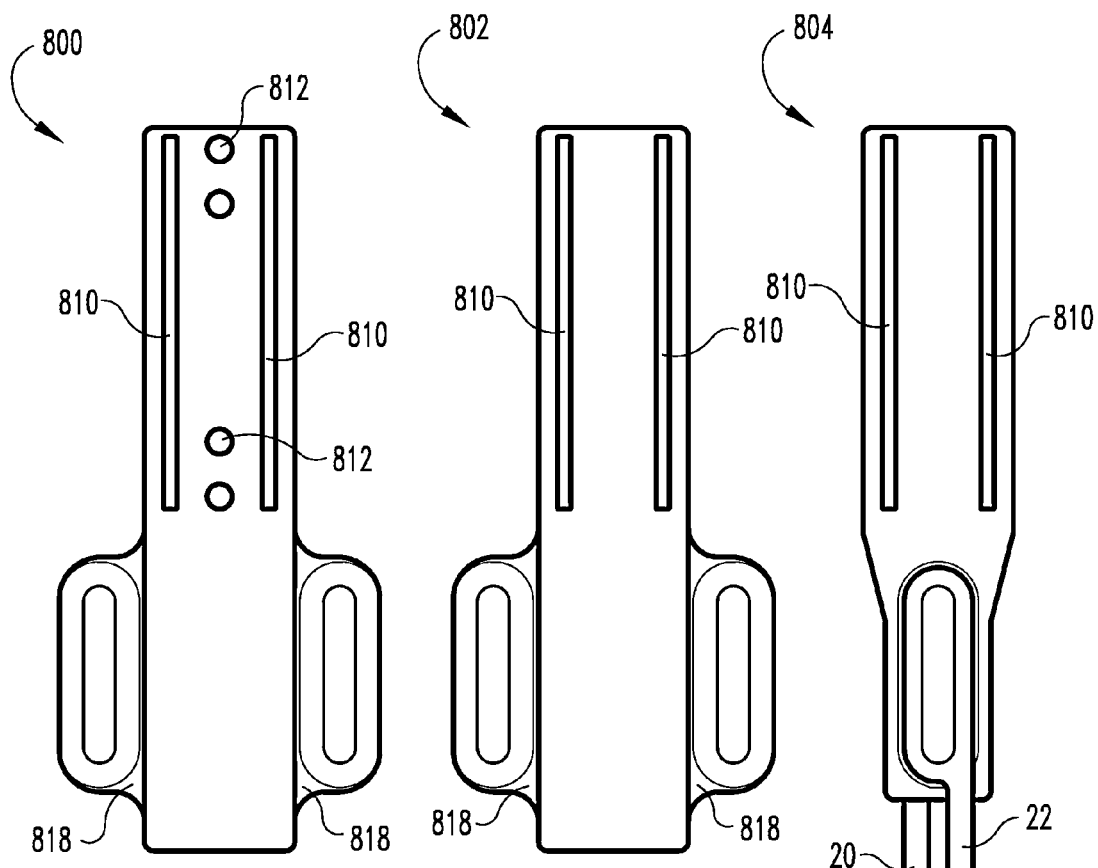
FIGS. 15A and 15B are bottom views of exemplary ablation rails in accordance with the instant disclosure.
Figure 15C:
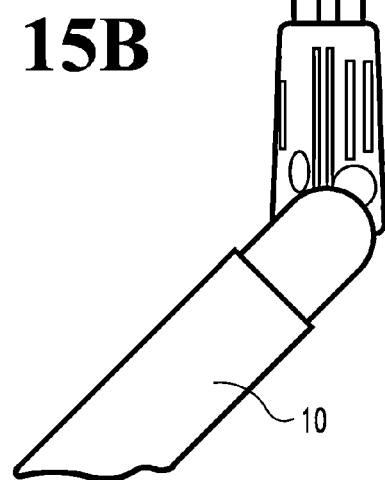
FIG. 15C is a profile view of an exemplary ablation rail in accordance with the instant disclosure, which is coupled to a robotic arm.

FIGS. 15A, 15B, and 15C illustrate exemplary linear ablation pens 800, 802, 804. Referring to FIG. 15A, the first linear ablation pen 800 includes at least one ablation electrode 810 and at least one recording electrode 812 that are in electrical communication with electrical contacts associated with the clamping area 818. In this exemplary embodiment, the clamping areas 818 extend laterally outward from a surface perpendicular to the electrode contact surface. Because there are at least two pair of clamping areas 818, the linear ablation pen 800 may be transferred from a first robotic arm (see, e.g., 10A in FIG. 9) to a second robotic arm (see, e.g., 10B in FIG. 9) without the pen 800 ever being uncoupled from the other robotic arm. In addition, multiple clamping areas 818 allow for repositioning of the pen 800 using one or both robotic arms. Alternatively, or in addition, the first robotic arm grasps the first clamping area 818 and is utilized for sensing electrical signals (such as those associated with the heart) by detecting current using the recording electrode 812. Concurrently, the second robotic arm grasps the second clamping area 818 and is utilized for powering the ablation electrode 810.

Referring to FIG. 15B, the second linear ablation pen 802 includes at least one ablation electrode 810 that is in electrical communication with electrical contacts associated with the clamping area 818. In this exemplary embodiment, the clamping areas 818 extend laterally outward from a surface perpendicular to the electrode contact surface. Because there are at least two pair of clamping areas 818, the linear ablation pen 802 may be transferred between a first robotic arm to a second robotic arm without the pen 802 ever being completely uncoupled from all robotic arms. In addition, multiple clamping areas 818 allow for repositioning of the pen 802 using one or both robotic arms.

Referring to FIG. 15C, the third linear ablation pen 804 includes at least one ablation electrode 810 that is in electrical communication with electrical contacts associated with the clamping area 818. In this exemplary embodiment, the clamping areas 818 extend laterally outward from a surface parallel to the electrode contact surface.

Figure 16:
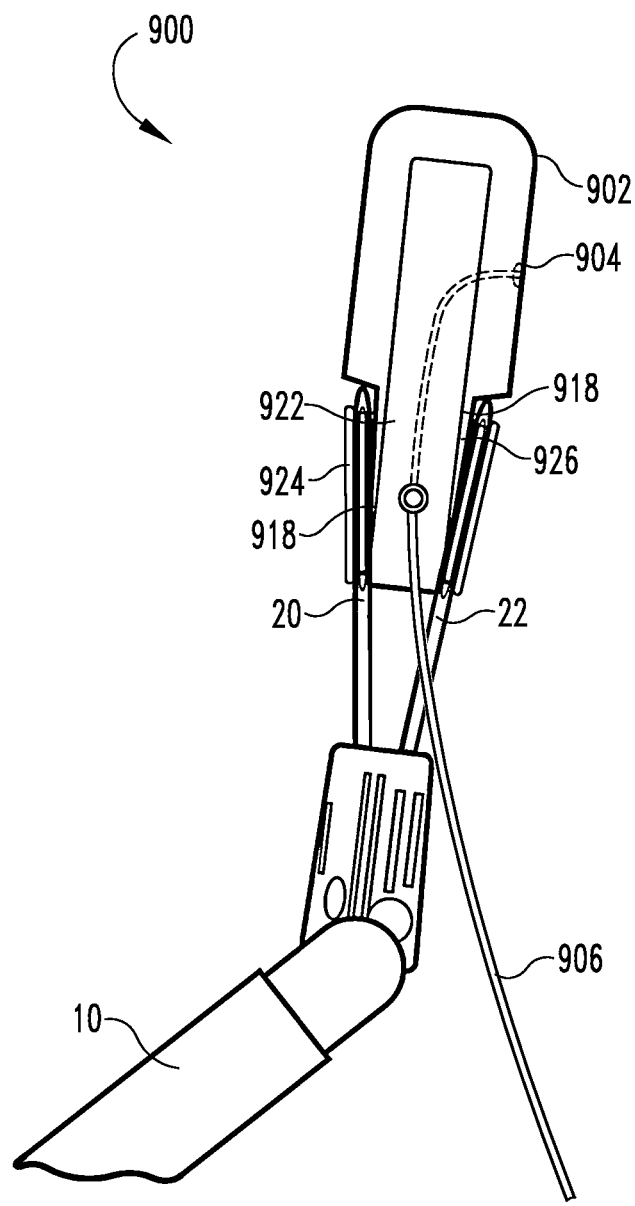
FIG. 16 is a profile view of an exemplary ablation and sensing device in accordance with the instant disclosure, which is coupled to a robotic arm.
Figure 17:
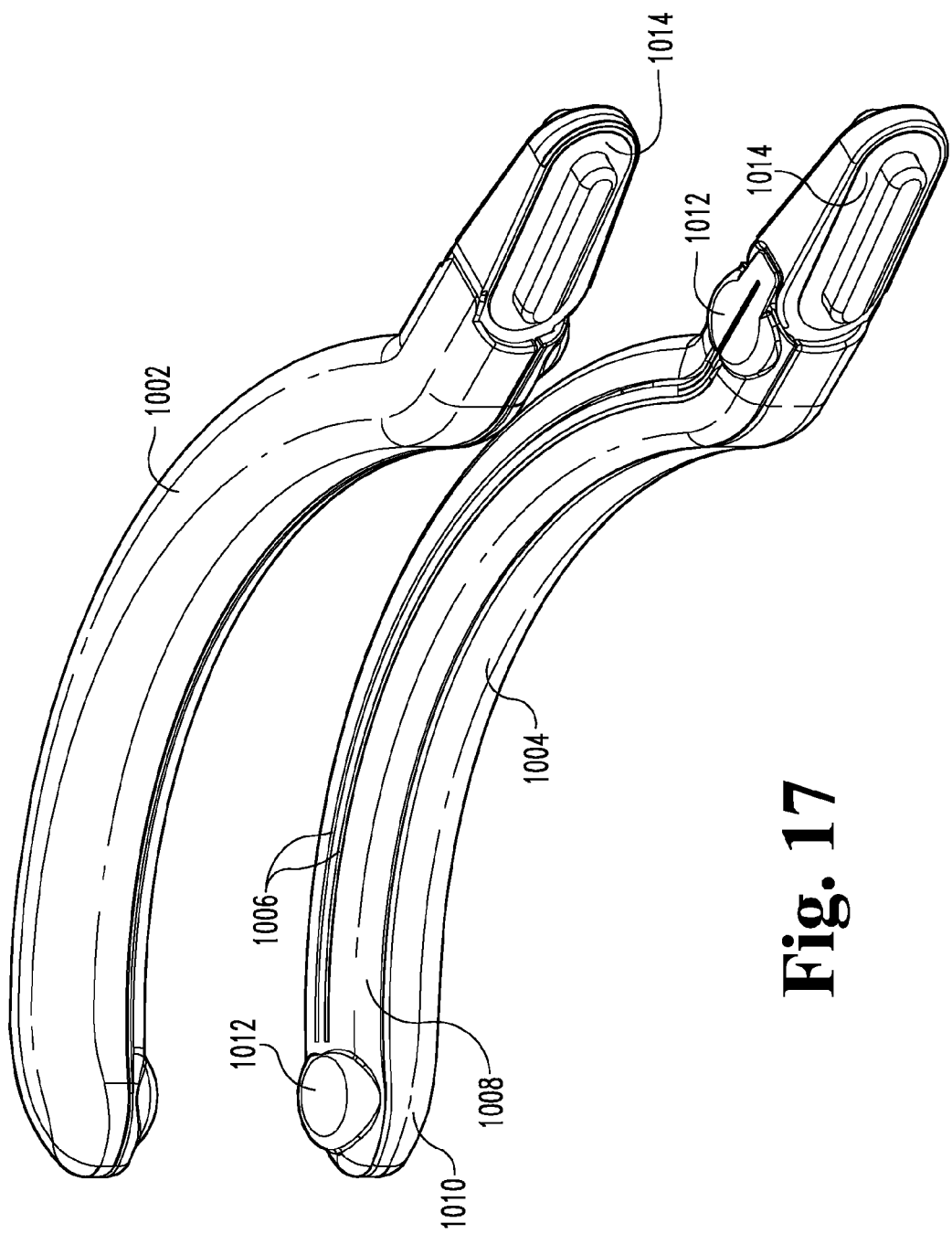
FIG. 17 is an elevated perspective view of the exemplary magnetic, bipolar ablation clamp in accordance with the instant disclosure.
Figure 18:
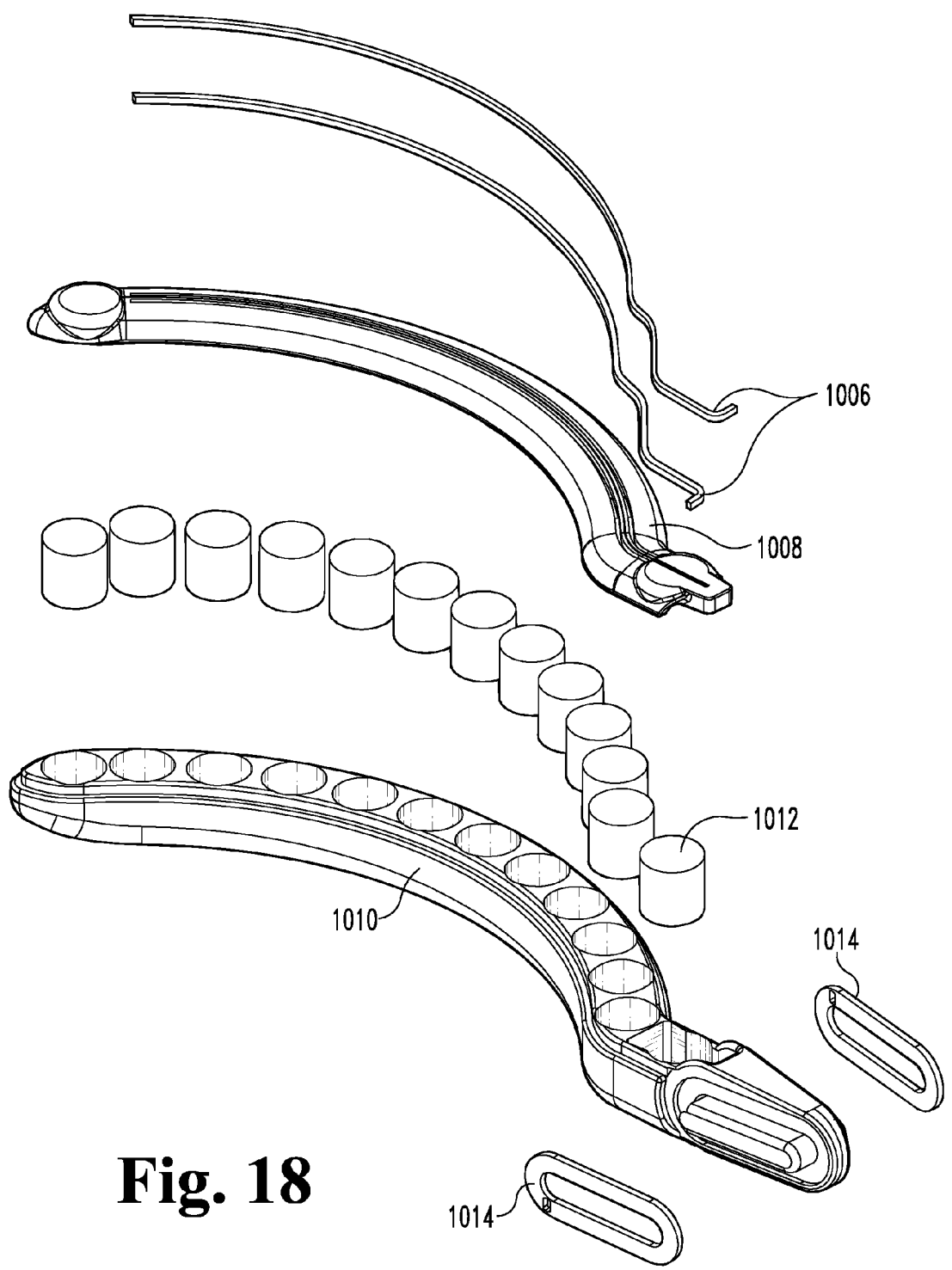
FIG. 18 is an exploded view of an exemplary jaw of the exemplary magnetic, bipolar ablation clamp of FIG. 17.
Figure 19:
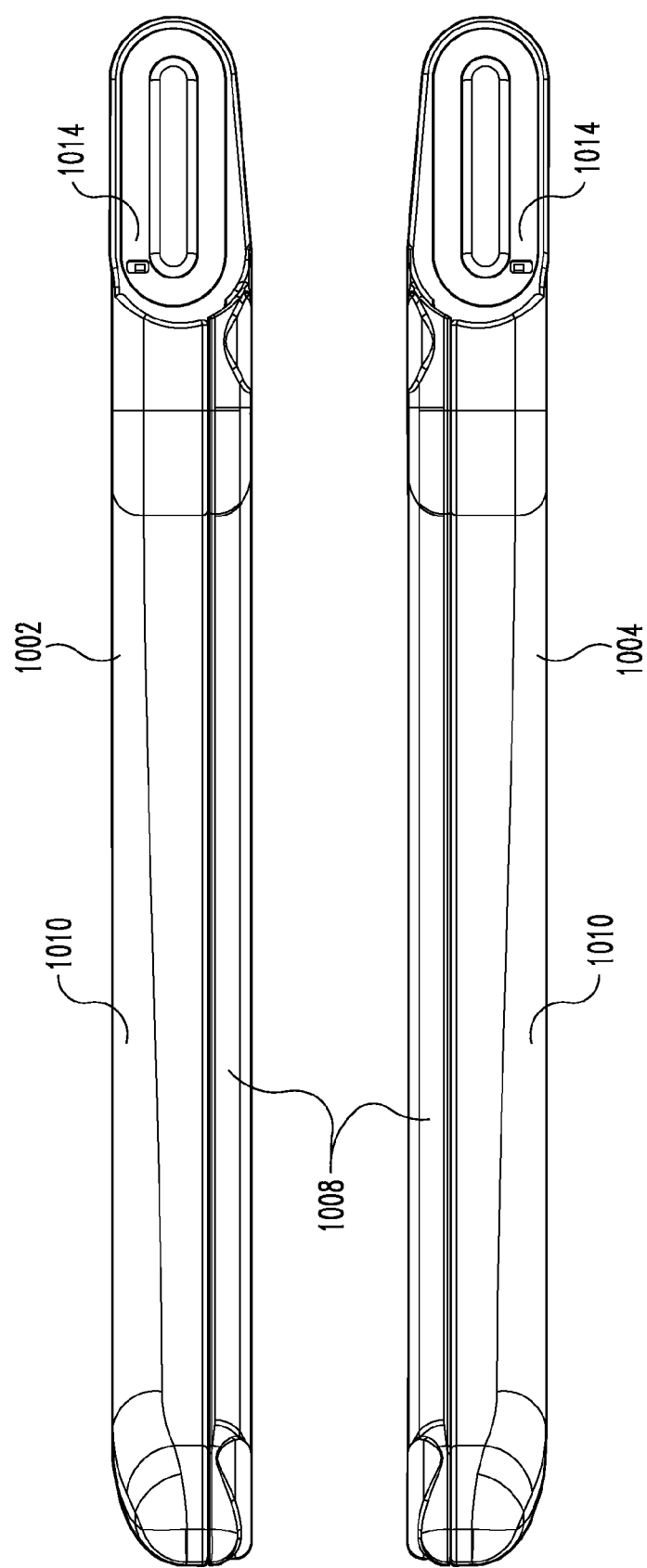
FIG. 19 is a profile view of the exemplary magnetic, bipolar ablation clamp of FIG. 17.
Figure 20:
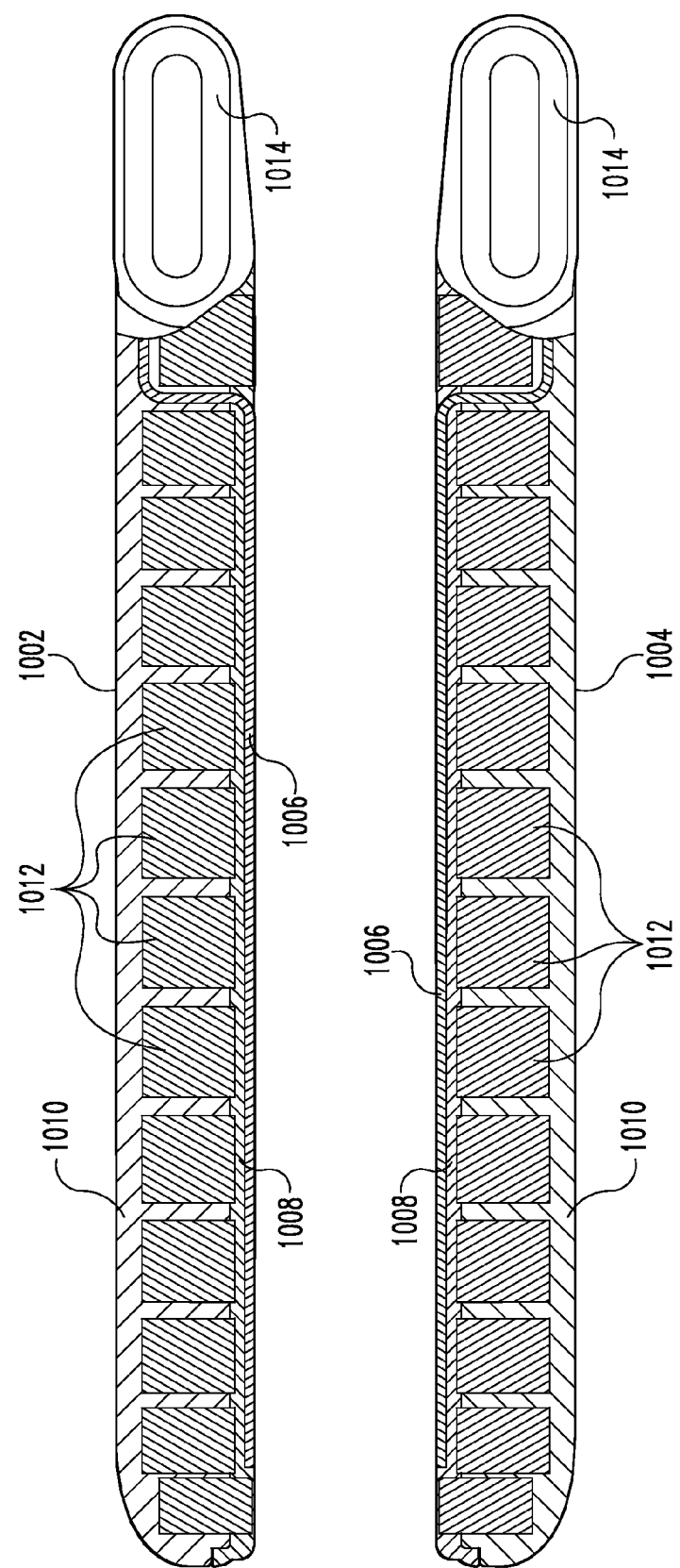
FIG. 20 is a longitudinal cross-sectional view of an exemplary magnetic, bipolar ablation clamp of FIG. 17.
Figure 21:
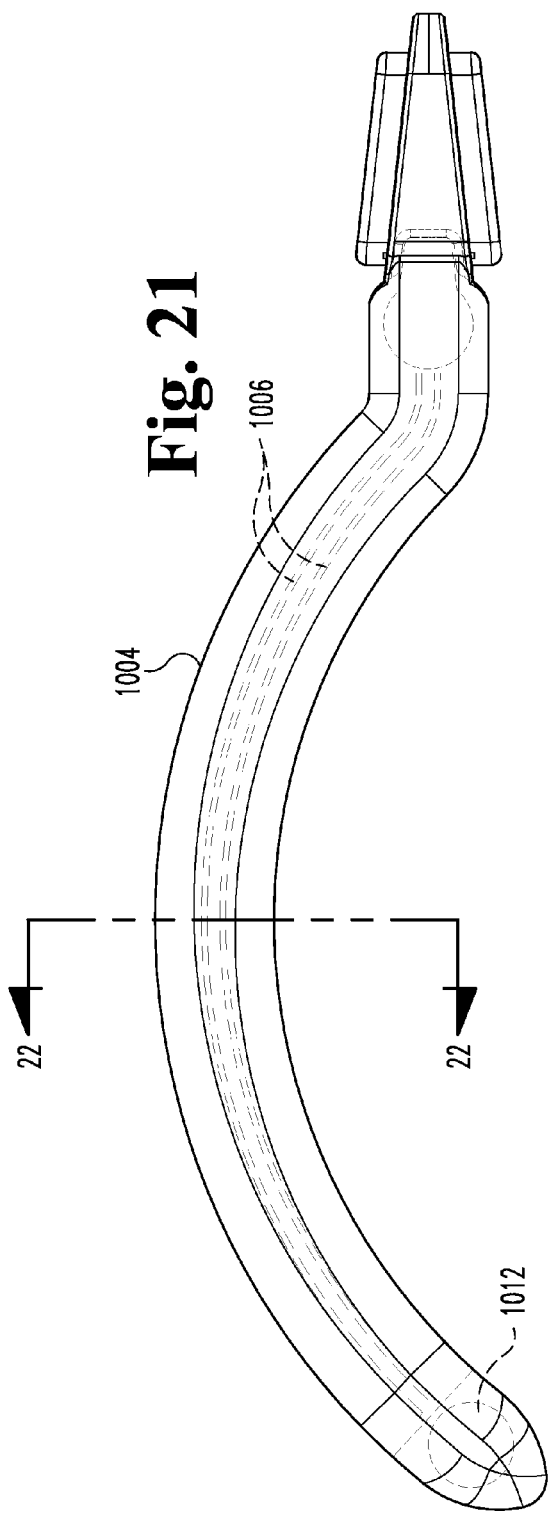
FIG. 21 is an overhead view of the exemplary jaw of the exemplary magnetic, bipolar ablation clamp of FIG. 17.
Figure 22:
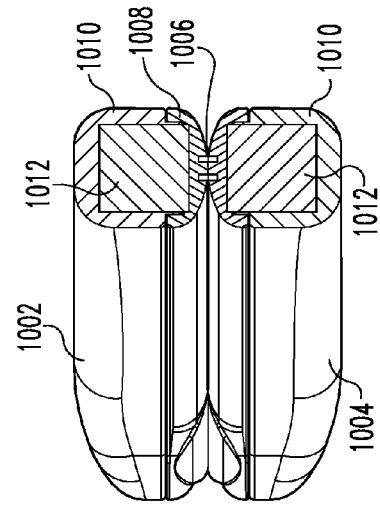
FIG. 22 is a cross-sectional view of the exemplary magnetic, bipolar ablation clamp of FIG. 21 taken along line A-A.
Figure 27:
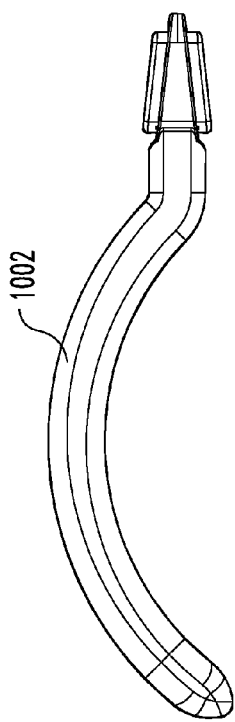
FIG. 27 is an overhead view of the exemplary magnetic, bipolar ablation clamp of FIG. 17 in the closed position.
Figure 28:
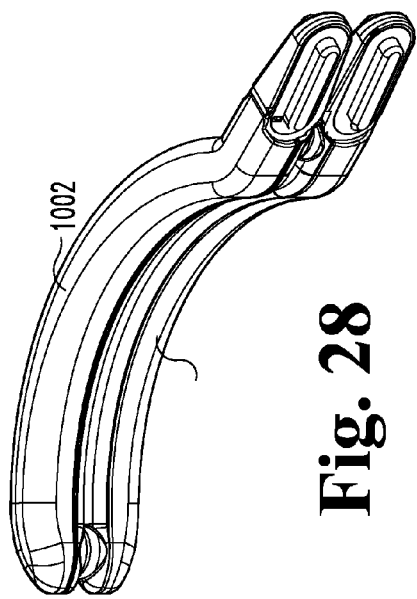
FIG. 28 is an elevated perspective view of the exemplary magnetic, bipolar ablation clamp of FIG. 17 in the closed position.
Figure 30:
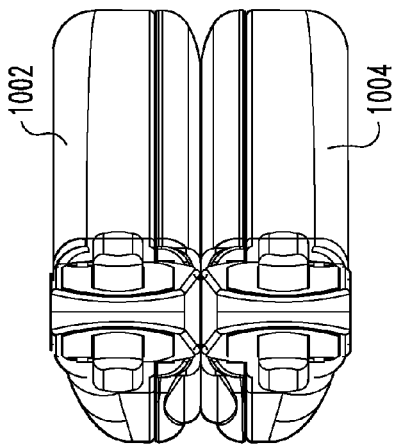
FIG. 30 is an end view of the exemplary magnetic, bipolar ablation clamp of FIG. 17 in the closed position.
Figure 29:
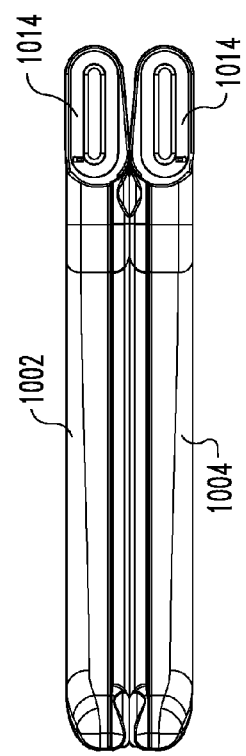
FIG. 29 is a profile view of the exemplary magnetic, bipolar ablation clamp of FIG. 17 in the closed position.

FIG. 16 illustrates an exemplary ablation and sensing device 900 that is mounted to a robotic arm 10. The ablation and sensing device 900 includes clamping areas 918 that engages the jaws 20, 22 of the robotic arm 10 in order to establish physical and electrical communication between a remote power source (not shown) and an ablation electrode 902. At least one sensing electrode 904 is also mounted to the ablation and sensing device 900. A tether 906 extends between the sensing electrode 904 and an external monitoring device (not shown) in order for the electronic monitoring device to receive signals from the sensing electrode.

Repositioning of the ablation and sensing device 900 and energizing the ablation electrode 902 are both controlled by the robotic arm 10 mounted thereto. Consistent with the foregoing embodiments, the jaws 20, 22 of the robotic arm 10 must be properly seated on the pads 926. To do this, the jaws 20, 22 are opened so that the oblong opening 24 of each jaw is aligned with and overlies one of the oblong projections 924 of the ablation and sensing device 900. Thereafter, the jaws 20, 22 are moved toward one another so that the oblong projections 924 pierce the openings 24 of the jaws 20, 22, thereby orienting the jaws 20, 22 to circumscribe the projections and ultimately sandwich the base 922 therebetween in a compression fit. This compression fit also establishes electrical communication between the contacts of the jaws 20, 22 and the contacts of the pads 926, which ultimately establishes electrical communication between the ablation electrode 902 and an external power source (not shown). As a result, when electrical power is supplied by the electrical power source, energizing of the ablation electrode 902 at the distal tip of the ablation and sensing device 900 occurs.

Referring to FIGS. 17-30, an exemplary magnetic, bipolar ablation clamp 1000 utilizes two separate clamping jaws 1002, 1004, with each respective clamping jaw being controlled by a separate robotic arm with grasping jaws 20, 22 (i.e., endoscopic graspers). Each clamping jaw 1002, 1004 includes at least one electrode 1006, insulative contact surfaces 1008, and a support frame 1010. Within each jaw 1002, 1004 are a series of magnets 1012 used to couple one jaw to another. Each electrode 1006 communicates with a contact 1014, which in turn engages with the electrode 40 of the jaws 20, 22 of the robotic arm 10 to create an electrical pathway extending between the electrodes 1006 and the electric source, such as an electric generator (not shown).

In use, the jaws 1002, 1004 are positioned on either side of the tissue to be ablated. One or both jaws 1002, 1004 are released from the robotic arms 10A, 10B, thereby allowing the magnet 1012 to couple the jaws 1002, 1004 about the tissue. The jaws 1002, 1004 are re-engaged by the respective robotic arms 10A, 10B in order to establish electrical communication between the electrodes 40 of the robotic jaws 20, 22 and the contacts 1014 of the respective jaws 1002, 1004 that are in electrical communication with the electrodes 1006. Thereafter, electric energy is delivered to the electrodes 40 of the robotic jaws 20, 22 to provide electric current to the electrodes 1006, thus ablating the tissue in contact with the electrodes 1006.

Figure 31:
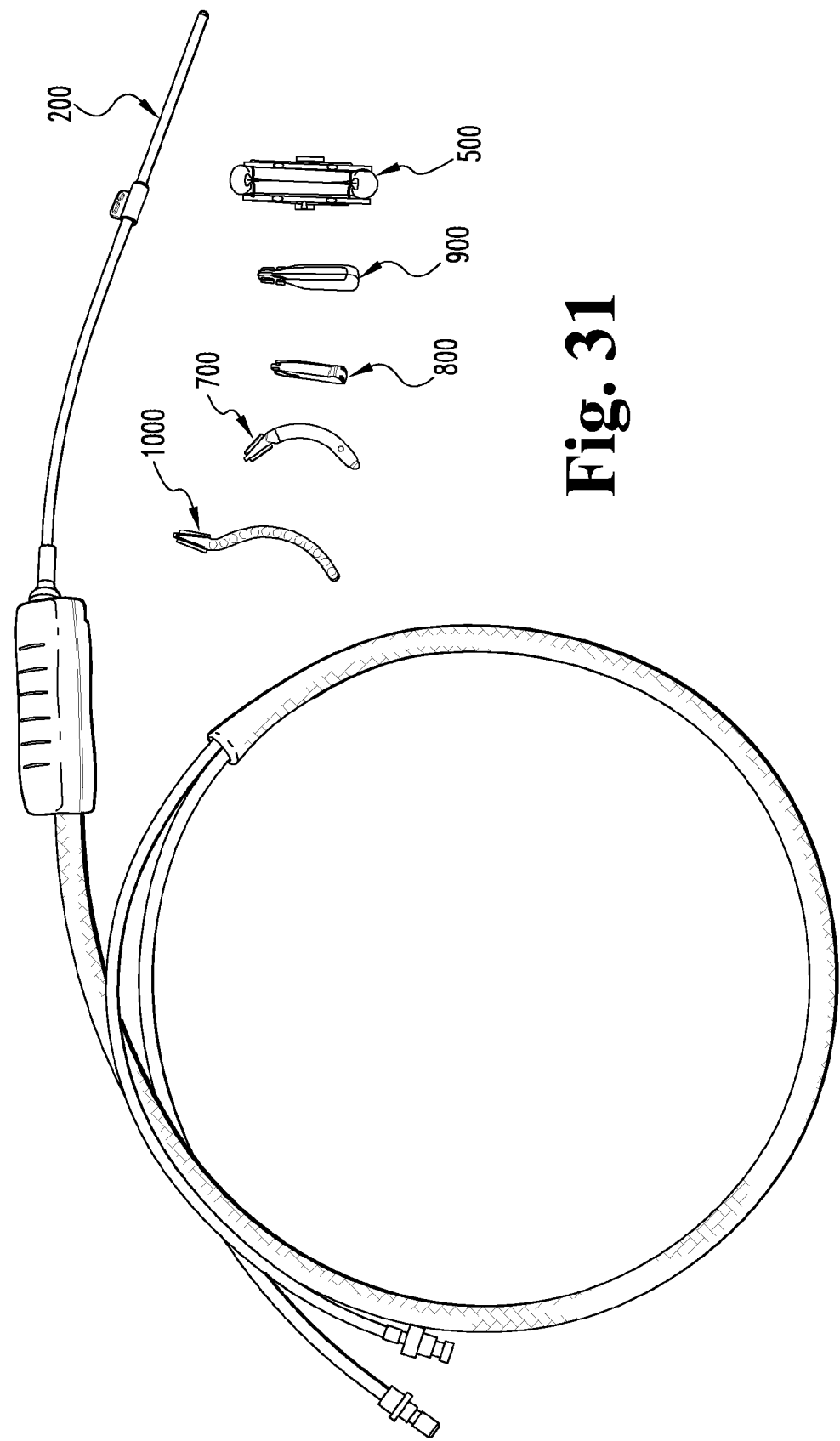
FIG. 31 is a photograph of an exemplary robotic toolkit in accordance with the instant disclosure.

Referring to FIG. 31, an exemplary robotic toolkit is shown that comprises an exemplary cryosurgical probe 200 (with or without a swivel—see Appendix I), an exemplary occlusion clip applicator 500, 530 (including those disclosed in Appendix II), an exemplary illuminated dissector 700, an exemplary ablation pen 800, another ablation pen/rail 900, and an exemplary magnetic, bipolar ablation clamp 1000.

Figure 32:
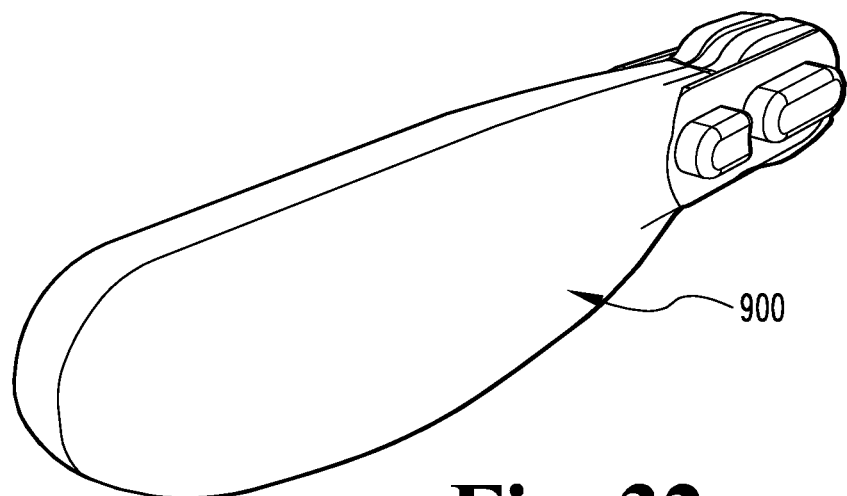
FIG. 32 is a photograph of the exemplary ablation pen/rail.

FIG. 32 is a photograph of the exemplary ablation pen/rail 900.

Figure 33:
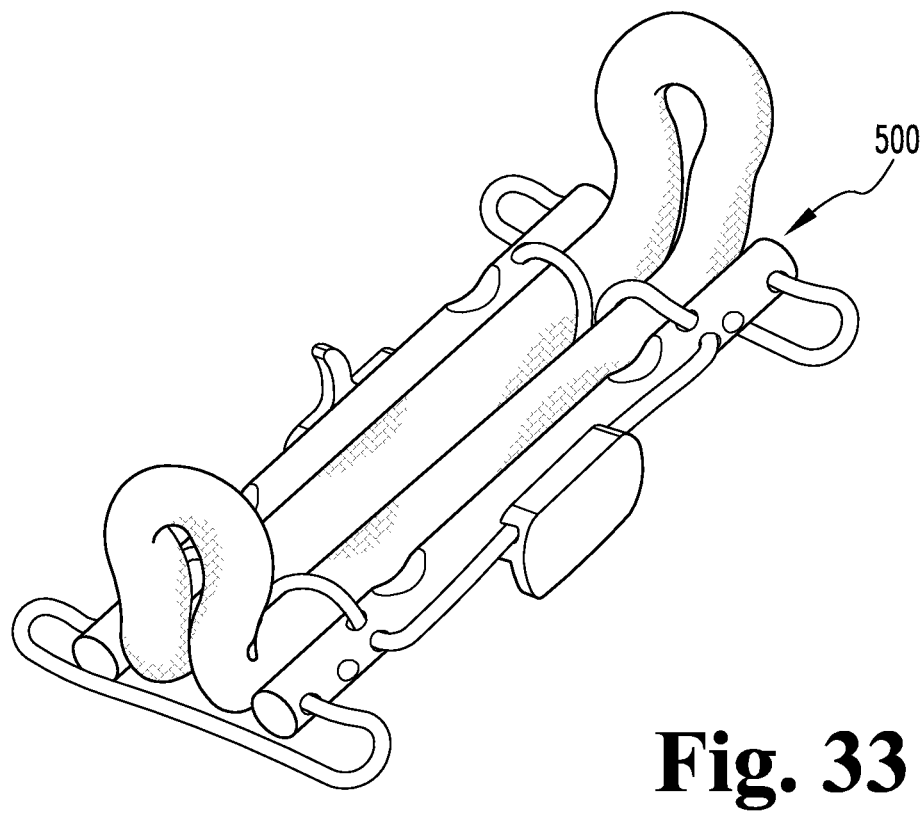
FIG. 33 is a photograph of the exemplary occlusion clip applicator.

FIG. 33 is a photograph of the exemplary occlusion clip applicator 500.

Figure 34:
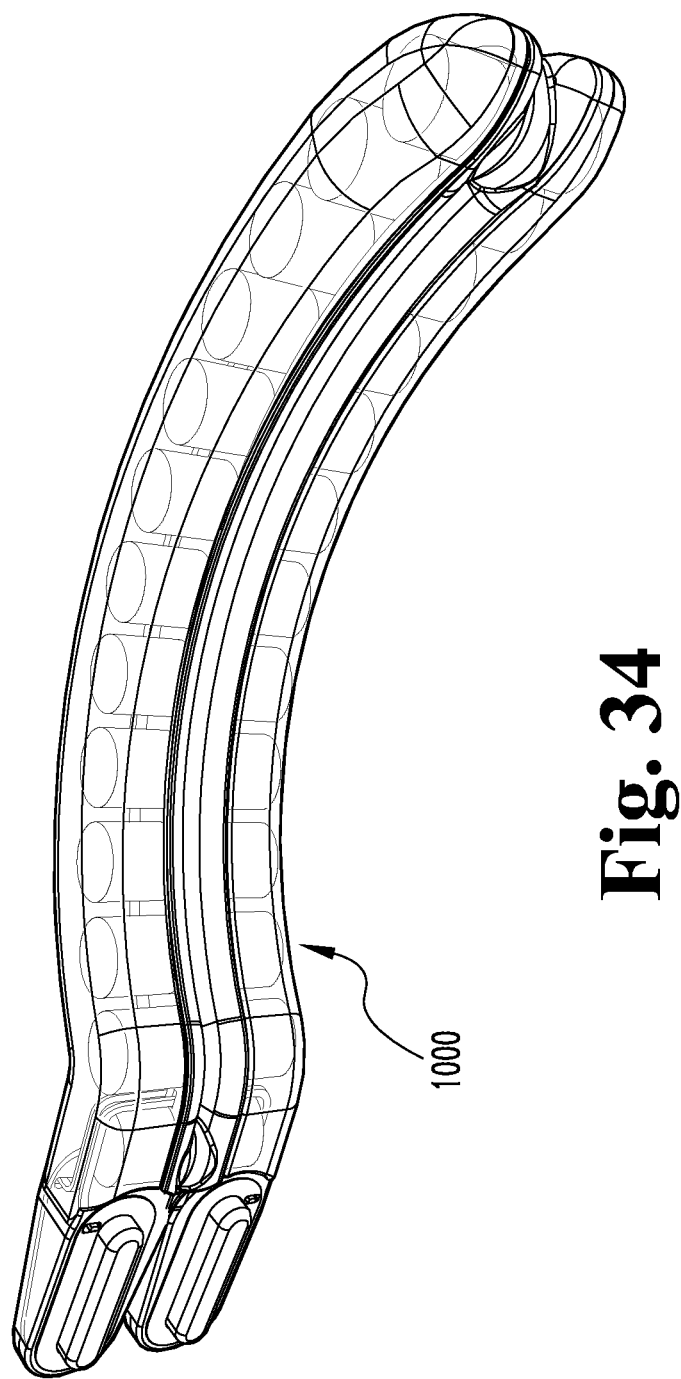
FIG. 34 is a photograph of the exemplary magnetic, bipolar ablation clamp.

FIG. 34 is a photograph of the exemplary magnetic, bipolar ablation clamp 1000.

Figure 35:
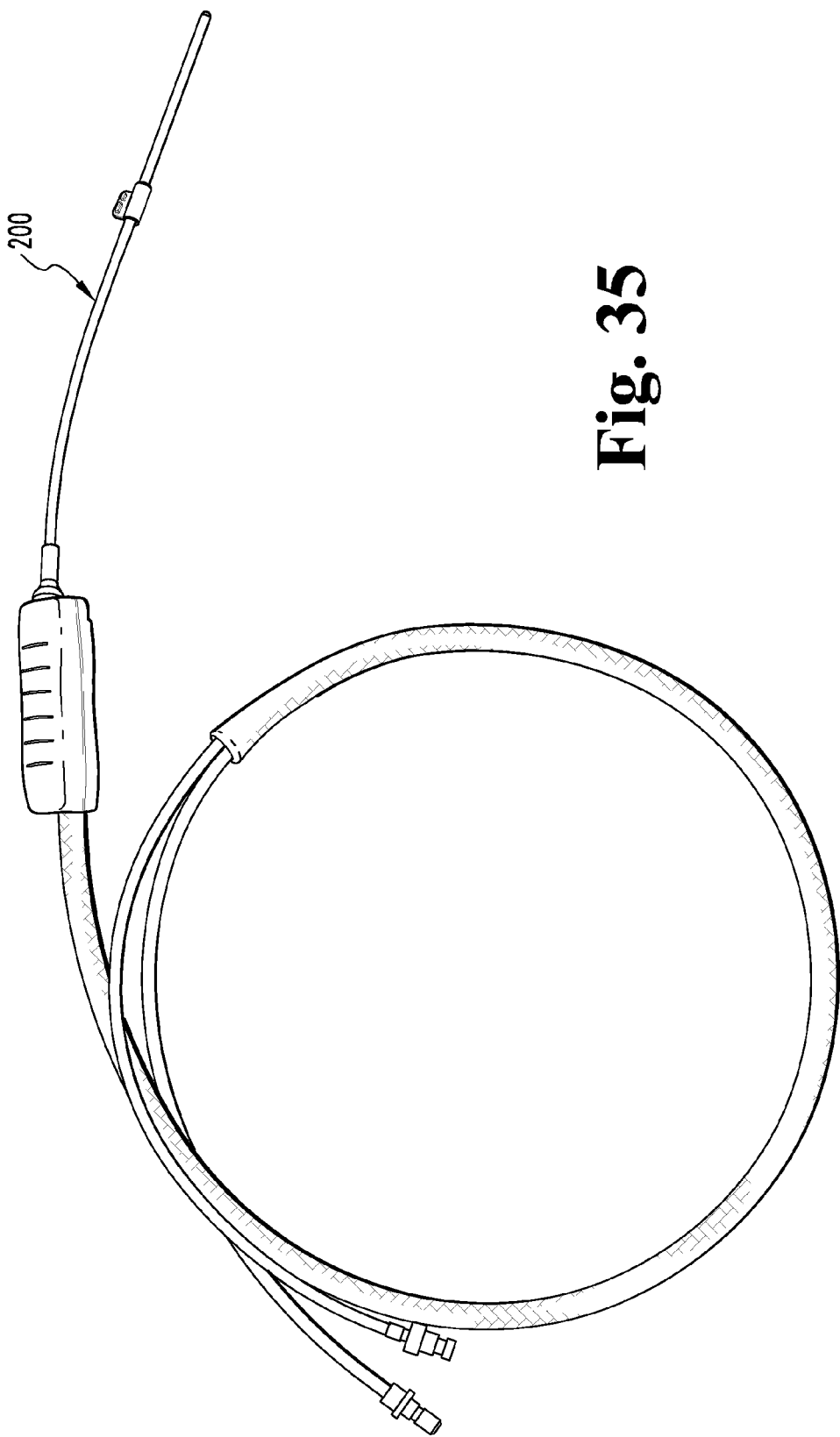
FIG. 35 is a photograph of the exemplary cryosurgical probe.

FIG. 35 is a photograph of the exemplary cryosurgical probe 200.

Figure 36:
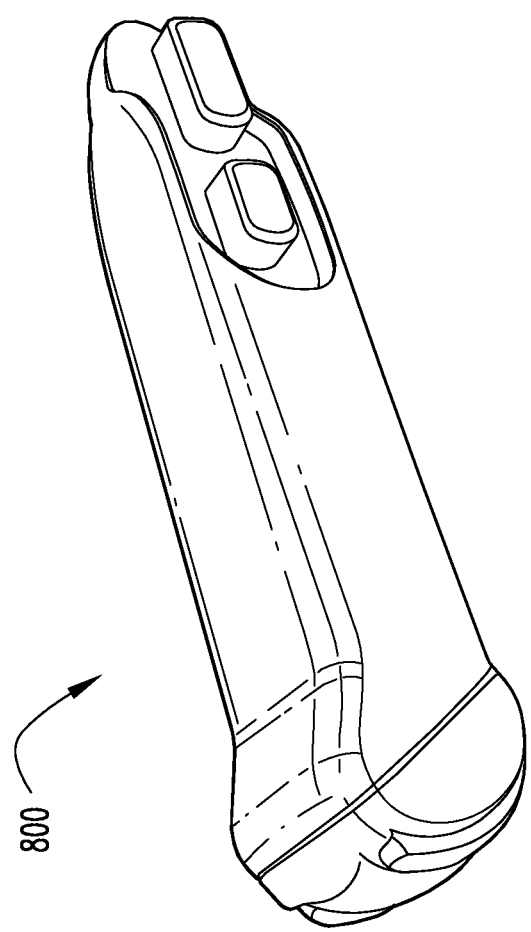
FIG. 36 is a photograph of the exemplary ablation pen.

FIG. 36 is a photograph of the exemplary ablation pen 800.

Figure 37:
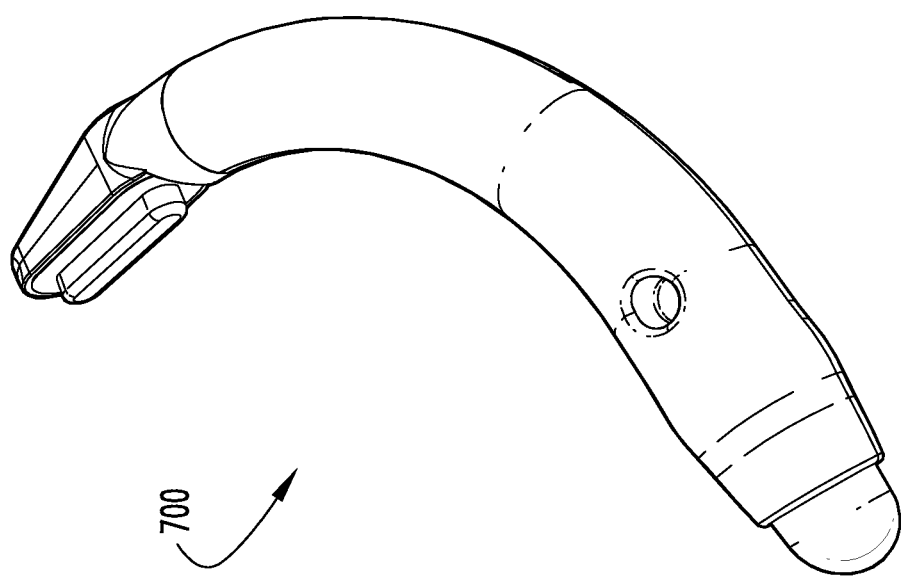
FIG. 37 is a photograph of the exemplary illuminated dissector.

FIG. 37 is a photograph of the exemplary illuminated dissector 700.

While the surgical instruments have been described in terms of those particularly appropriate for cardiac applications, this is not by way of limitation, but for illustration. Indeed, any surgical instruments adapted for use with robotic devices may advantageously include the clamping area described above.

Following from the above description and embodiment, it should be apparent to those of ordinary skill in the art that, while the foregoing constitutes an exemplary embodiment of the present disclosure, the disclosure is not necessarily limited to this precise embodiment and that changes may be made to this embodiment without departing from the scope of the invention as defined by the claims. Additionally, it is to be understood that the invention is defined by the claims and it is not intended that any limitations or elements describing the exemplary embodiment set forth herein are to be incorporated into the interpretation of any claim element unless such limitation or element is explicitly stated. Likewise, it is to be understood that it is not necessary to meet any or all of the identified advantages or objects of the disclosure discussed herein in order to fall within the scope of any claims, since the invention is defined by the claims and since inherent and/or unforeseen advantages of the present disclosure may exist even though they may not have been explicitly discussed herein.

What is claimed is:

1. A cryosurgical probe comprising:
   an elongated metal tube including a proximal portion and a distal portion;
   a cryogenic fluid supply conduit disposed on an interior of the elongated metal tube, the cryogenic fluid supply conduit including at least one outlet orifice;
   an electrical load associated with the elongated metal tube; and,
   an electrical contact associated with the elongated metal tube and in electrical communication with the electrical load via an electrical lead.

2. The cryosurgical probe of claim 1, wherein the electrical load comprises an electronically controlled valve in series with the cryogenic fluid supply conduit.

3. The cryosurgical probe of claim 2, wherein the electronically controlled valve is housed within the elongated metal tube.

4. The cryosurgical probe of claim 2, wherein the electronically controlled valve is housed within a housing separate from the elongated metal tube.

5. The cryosurgical probe of claim 1, wherein the electrical contact is operatively coupled to the elongated metal tube and comprises a dedicated projection extending from an exterior of the elongated metal tube.

6. The cryosurgical probe of claim 1, wherein the electrical contact comprises a plurality of electrical contacts.

7. The cryosurgical probe of claim 6, wherein the plurality of electrical contacts comprise bipolar contacts.

8. The cryosurgical probe of claim 1, wherein the at least one outlet orifice of the cryogenic fluid supply conduit comprises a plurality of outlet orifices.

9. The cryosurgical probe of claim 8, wherein the plurality of outlet orifices are spaced apart along a dominant longitudinal dimension of the elongated metal tube.

10. The cryosurgical probe of claim 9, wherein:
    the cryogenic fluid supply conduit comprises a plurality of cryogenic fluid supply conduits; and,
    each of the plurality of cryogenic fluid supply conduits includes at least one of the plurality of outlet orifices.

11. The cryosurgical probe of claim 10, wherein the plurality of cryogenic fluid supply conduits are staggered within the elongated metal tube along the dominant longitudinal dimension of the elongated metal tube.

12. The cryosurgical probe of claim 1, wherein the distal portion of the elongated metal tube includes a closed end.

13. The cryosurgical probe of claim 1, wherein the elongated metal tube includes a swivel.

14. A method of operating a surgical instrument, the method comprising:
coupling an electrical terminal of a first robotic arm to a first electrical contact of a first separable surgical tool head, the first separable surgical tool head including a first electrical load in electrical communication with the first electrical contact, wherein coupling the electrical terminal to the first electrical contact establishes electrical communication between the electrical terminal and the first electrical load;
supplying electric power to the electrical terminal after coupling of the electrical terminal to the first electrical contact;
conveying the electric power to the first electrical load via the first electrical contact;
consuming the electric power by the first electrical load as part of carrying out a surgical procedure; and,
repositioning the first separable surgical tool head using the first robotic arm after coupling the electrical terminal of the first robotic arm to the first electrical contact of the first separable surgical tool head, wherein the first separable surgical tool head comprises:
an elongated metal tube including a proximal portion and a distal portion;
a cryogenic fluid supply conduit disposed on an interior of the elongated metal tube, the cryogenic fluid supply conduit including at least one outlet orifice;
an electrical load associated with the elongated metal tube; and,
an electrical contact associated with the elongated metal tube and in electrical communication with the electrical load via an electrical lead.

15. The method of claim 14, wherein:
the electrical load comprises an electronically controlled valve in series with the cryogenic fluid supply conduit; and,
the act of consuming the electric power by the first electrical load as part of carrying out the surgical procedure includes actuating the electronically controlled valve to distribute cryogenic fluid to the interior of the elongated metal tube.

16. The method of claim 15, further comprising contacting an exterior of the elongated metal tube with tissue to ablate the tissue responsive to actuating the electronically controlled valve to distribute cryogenic fluid to the interior of the elongated metal tube.

* * * * *